United States Patent
Keen

(10) Patent No.: US 12,110,261 B2
(45) Date of Patent: Oct. 8, 2024

(54) FREE RADICAL PROCESS FOR MAKING LOW MOLECULAR WEIGHT COMPOUNDS USEFUL FOR MAKING HIGH OCTANE FUELS

(71) Applicant: Keen Process Technologies, LLC, Pinch, WV (US)

(72) Inventor: Brian T. Keen, Pinch, WV (US)

(73) Assignee: Keen Process Technologies, LLC, Pinch, WV (US)

( * ) Notice: Subject to any disclaimer, the term of this patent is extended or adjusted under 35 U.S.C. 154(b) by 551 days.

(21) Appl. No.: 17/256,767

(22) PCT Filed: Jul. 15, 2019

(86) PCT No.: PCT/US2019/041792
§ 371 (c)(1),
(2) Date: Dec. 29, 2020

(87) PCT Pub. No.: WO2020/018415
PCT Pub. Date: Jan. 23, 2020

(65) Prior Publication Data
US 2021/0269378 A1 Sep. 2, 2021

Related U.S. Application Data

(60) Provisional application No. 62/698,476, filed on Jul. 16, 2018.

(51) Int. Cl.
*C07C 2/56* (2006.01)
*C07C 29/44* (2006.01)
*C10L 1/04* (2006.01)

(52) U.S. Cl.
CPC ............... *C07C 2/56* (2013.01); *C07C 29/44* (2013.01); *C10L 1/04* (2013.01)

(58) Field of Classification Search
CPC .. C07C 2/56; C07C 29/44; C10L 1/04; C10G 29/205
See application file for complete search history.

(56) References Cited

U.S. PATENT DOCUMENTS

| | | | |
|---|---|---|---|
| 2,562,217 A | 7/1951 | Schmerling | |
| 2,668,181 A * | 2/1954 | Fitz Gerald | C07C 29/44 568/904 |
| 2,834,818 A | 5/1958 | Schmerling et al. | |
| 3,278,562 A | 10/1966 | Thigpen et al. | |
| 3,773,843 A | 11/1973 | Schmerling et al. | |
| 3,821,298 A | 6/1974 | Cywinski | |
| 4,156,101 A | 5/1979 | Erchak et al. | |
| 5,095,168 A | 3/1992 | Kranz | |
| 5,856,592 A | 1/1999 | Hagen | |
| 7,977,520 B2 | 7/2011 | Borgmann et al. | |
| 8,558,030 B2 | 10/2013 | Briggs et al. | |
| 8,779,164 B2 | 7/2014 | Leeuwen et al. | |
| 8,912,346 B2 | 12/2014 | Leeuwen et al. | |
| 10,023,513 B1 | 7/2018 | Keen | |
| 2012/0009090 A1 | 1/2012 | Gadewar et al. | |
| 2017/0022126 A1 * | 1/2017 | Mukherjee | C07C 9/16 |

OTHER PUBLICATIONS

Wikipedia, "Alkylation unit", https://en.wikipedia.org/w/index.php?title=Alkylation_unit&oldid=980681063, Last edited on Sep. 27, 2020, 11 pgs.
EIA, U.S. Energy Information Administration, Today in Energy "Alkylation is an important source for octane in gasoline", https://www.eia.gov/todayinenergy/detail.php?id=9971, Feb. 13, 2013, 2 pgs.
Dupont, Shane Presley, DuPont Clean Technologies, "Meeting Octane Demand Through Technology Conversion, A Better, Safer, Cleaner Path Forward", 2017, 4 pgs.
Wikipedia, "Octane rating", https://en.wikipedia.org/wiki/Octane_rating, Last edited on Dec. 29, 2020, 18 pgs.
International Application No. PCT/US2019/041792, "Notification of Transmittal of the International Search Report and the Written Opinion of the International Searching Authority" Nov. 22, 2019, 13 pgs.

* cited by examiner

*Primary Examiner* — Ali Z Fadhel
(74) *Attorney, Agent, or Firm* — Kagan Binder PLLC

(57) ABSTRACT

The present invention relates to free radical reaction methods in which low molecular weight, C2 to C6, unsaturated organic compounds such as ethylene and/or propylene are reacted with low molecular weight, C1 to C15, preferably C1 to C10 saturated organic compounds to form low molecular weight, linear or branched C3 to C24, preferably C3 to C12 organic compounds. The present invention is based at least in part upon the concept of carrying out the free radical reaction in the presence of a typically low concentrations of the unsaturated reactant(s) in the reaction zone(s). By doing this, chain transfer mechanisms are more favored while chain extension mechanisms are less favored. In some embodiments, principles of the present invention are helpful to create conditions under which chain transfer to form more stable, secondary or tertiary branched radicals is favored over olefin addition via chain extension.

18 Claims, No Drawings

FREE RADICAL PROCESS FOR MAKING LOW MOLECULAR WEIGHT COMPOUNDS USEFUL FOR MAKING HIGH OCTANE FUELS

PRIORITY CLAIM

The present application claims priority to international application no. PCT/US2019/041792, filed Jul. 15, 2019, which in turn claims priority to United States Provisional Patent Application having Ser. No. 62/698,476, filed on Jul. 16, 2018, by Brian T. Keen and titled FREE RADICAL PROCESS FOR MAKING LOW MOLECULAR WEIGHT COMPOUNDS USEFUL FOR MAKING HIGH OCTANE FUELS, wherein the entireties of which are respectively incorporated herein by reference for all purposes.

FIELD OF THE INVENTION

The present invention relates to free radical reaction methods in which low molecular weight, C2 to C6, unsaturated organic compounds such as ethylene and/or propylene are reacted with low molecular weight, C1 to C15, preferably C1 to C10 saturated organic compounds to form low molecular weight C3 to C24, preferably C3 to C12 organic compounds. In some aspects, the present invention is useful to prepare C5 to C12 branched organic compounds with high octane number. Such branched products are useful as high octane motor fuel or as additives to boost the octane rating of motor fuels. In other aspects, the present invention is useful to prepare low molecular weight, linear C3 to C12, or even C3 to C5 alcohols from inexpensive starting materials such as ethylene and propylene on the one hand, and methanol or ethanol on the other hand. In other aspects, the present invention is useful to prepare less branched C6 to C24 organic compounds useful in diesel fuel formulations.

BACKGROUND OF THE INVENTION

Free radical reaction chemistry includes any chemical reaction that involves free radicals as reactants, intermediates, or products. A free radical reaction typically takes place in the presence of a free radical initiator. Free radical reactions often involve a chain reaction in which one or more steps involve bond dissociation of C—H bonds to produce radicals. Bond dissociation energies within the range from 84 kcal/mol to 98 kcal/mole tend to be more suitable for producing radicals in these reactions. Free radical chemistry is further described in U.S. Pat. Nos. 8,912,346; 8,779,164; 8,558,030; and 7,977,520. Bond dissociation energies of many hydrogen bonds is reported in Yu-Ran Lo, *Handbook of Bond Dissociation Energies in Organic Compounds*, CRC Press; 1 edition (Dec. 26, 2002).

One kind of free radical reaction occurs between one or more unsaturated compounds and one or more additional co-reactive substances that react according to the following schematic reaction:

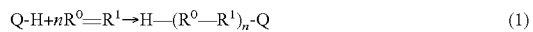
(1)

wherein Q represents an organic moiety, the single bond(s) between the Q and H has a bond dissociation energy often in the range from 84 kcal/mol to 98 kcal/mole, each of $R^0$ and $R^1$ independently is an organic moiety, $R^0$ and $R^1$ in $R^0=R^1$ are linked by a carbon-carbon double bond (e.g., $R^0=R^1$ is ethylene, propylene, and/or other olefins in many instances); and —($R^0$—$R^1$)— schematically represents a divalent organic moiety (e.g., an alkylene moiety when $R^0=R^1$ is ethylene, propylene, and/or other olefins) corresponding to $R^0=R^1$; and n is 1 or more, preferably 1 or 2, more preferably 1.

In some instances according to conventional free radical chemistry practices, the Q-H bond may involve a bond between H and a primary carbon atom, as chain extension steps are strongly favored in the free radical chain reaction. This is due in part to the high reactivity (non-selectivity) of some initiators and the higher availability of primary carbon hydrogen. In some instances according to conventional free radical chemistry practices, it has been difficult to control chain extension. The result often has been that n is very diverse and even 100 or more on average. It would be desirable to carry out this reaction either to be able to increase the amount of product for which n is 1 to 6, preferably 1 or 2, or even preferably 1, in a manner effective to produce substantially linear or branched products of limited weight, those with 3 to 24 carbon atoms, preferably 5 to 12 carbon atoms. In some modes of practice, it also would be desirable to carry out this reaction to improve the ability to react the unsaturated reactant with Q-H bonds in which the H is bonded to a secondary or tertiary carbon atom. This would increase the amount of branched product compounds that result even when using linear starting reactants. It also would be desirable to add residues of ethylene onto the C1 to C15 organic reactant(s) in a linear and limited manner to provide C6 to C24 compounds useful in the formulation of diesel fuel. It also would be desirable to produce a substantial amount of products per gram of initiator used for the reaction.

It also would be desirable to carry out this reaction to increase the amount of product for which a single unsaturated species adds to different spots on the Q moiety. Such a product would be represented by the following reaction scheme which for illustrative purposes shows unsaturated reactant being added to two different sites on the saturated reactant, although in some reactions it even may be desirable to add the unsaturated reactant to three or more sites:

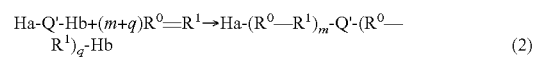
(2)

wherein Q' is an organic moiety; each Ha and Hb is a different hydrogen atom; each Q'-Ha and Q'-Hb bond has a bond dissociation energy often in the range from 84 kcal/mol to 98 kcal/mole; $R^o$, $R^1$, $R^0=R^1$, and —($R^0$—$R^1$)— are as defined above; and each of m and q independently is 0, 1 or 2, preferably 0 or 1 with the proviso that at least one of m and q is not 0 and the proviso that Ha and Hb are not attached to the same carbon. In preferred embodiments, at least one Q'-Ha or Q'-Hb bond involves the H being bonded with a secondary or tertiary carbon atom. As was the case for Equation (1), it also is desirable to produce a substantial amount of products per gram of initiator used for the reaction.

Each of the compounds Q-H or the compound Ha-Q'-Hb is referred to as a chain transfer agent and often is a saturated organic compound containing one or more free radically reactive C—H bonds with a suitable bond dissociation energy. Each of Q-H and Ha-Q'-Hb represents a single chain transfer agent or a mixture of chain transfer agents if more than one kind of chain transfer agent is used. The unsaturated $R^0=R^1$ is referred to as an unsaturated reactant. The product H—($R^0$—$R^1$)$_n$-Q or Ha-($R^0$—$R^1$)$_m$-Q'-($R^0$—$R^1$)$_q$-Hb, as the case may be, is often a mixture of compounds of different chain lengths, e.g., compounds characterized by a variety of n, m, or q values, as the case may be, are produced.

Unfortunately, achieving these goals individually as well as at the same time has been challenging. For example, U.S. Pat. No. 2,668,181 describes a free radical process that requires excessive and uneconomical amounts of costly peroxide initiator (typically 0.1 to 0.3 moles per mole of product made) and typically produces less than 10 g of product per gram of initiator. The product mix also is undesirably diffuse and relatively high molecular weight. U.S. Pat. No. 4,156,101 also describes methods that give a low product yield per 1 gram of initiator and that result in a heavy complex non-selective product mixture.

Accordingly, there is a strong need for improved free radical reaction strategies that can produce linear or branched products of limited molecular weight more selectively relative to larger species, while at the same time also producing increased amounts of products per gram of initiator.

When olefins are reacted with hydrocarbon chain transfer agents to prepare higher molecular weight hydrocarbon products, the resulting products are referred to as alkylates in the oil refinery and motor fuel production industries. Alkylates and other free radical products with high octane number and limited molecular weight (e.g., C5 to C12 species) are highly desirable in order to help provide motor fuels with high octane number. Higher octane numbers generally indicate a greater ability of a fuel to withstand detonation under compression. Normally, fuel ignites when triggered by a spark plug. However, fuel with a low octane rating can self-ignite under compression in the absence of such a spark or before the main flame front reaches pockets of unburned fuel. This may produce shockwaves, higher pressure, and more heat that can undermine the performance of or seriously damage engines. In other words, the octane number of a fuel indicates the tendency of a fuel to burn in a controlled manner, with higher octane number or rating being indicative of better control. Fuels are formulated with high octane number to minimize the risk of undesired detonation upon compression. Generally, a high octane number of over 80, or even over 85, or even over 90 indicates a fuel that can burn in a controlled manner.

Currently, natural gas as well as base natural gasoline produced in refineries by various processes do not have sufficient octane rating to be directly used as motor vehicle fuel. Fuel additives may be blended into fuels to help boost the octane rating. Common additives used for this purpose include aromatic compounds such as toluene, C4 to C12, highly branched hydrocarbon alkylates such as isooctane (octane number of 100), and alcohols such as ethanol. Aromatic materials may pose safety/health exposure concerns, and alcohols boost octane but undermine fuel quality. Accordingly, alkylates are a highly desirable additive to boost octane rating.

Unfortunately, the synthesis of suitable linear or branched products of limited molecular weight, such as alkylates, has been problematic in terms of needing high quantities of highly hazardous and corrosive catalyst materials. In an exemplary situation, alkylates are produced in refineries by reacting isobutane and low molecular weight alkenes (primarily propene, butenes and sometimes pentenes) using concentrated sulfuric acid or hydrofluoric acid catalysts. The use of these extremely hazardous and corrosive acid catalysts results in significant handling, safety and environmental issues as well as high capital and operating costs. The alkylation processes are among the most hazardous in any oil refinery. An improved less hazardous and less costly process for production of high octane C4 to C12 alkylate is desired and would be welcomed by the industry.

Importantly, methane and natural gas liquids (NGL) such as ethane, propane and butane are present in high concentrations in Marcellus and other shale natural gas. However, those materials are too volatile to be used directly in typical vehicle fuels. Ethane in particular is problematic in that it is plentiful in some natural gas formations, cannot be liquefied easily, needs to be removed from the main methane stream, and thus is often stranded at natural gas compression stations due lack of pipelines for transport. It has long been desired to have an economical and efficient process for converting these C2 to C4 hydrocarbons to a C4 to C12 liquid hydrocarbon fuel (gasoline) or fuel additive. One process, said by some to be the best state of the art process currently, is based on the "Fischer-Tropsch" synthesis but is inefficient, requires both a large economy of scale as well as a massive capital investment to be marginally commercially viable [https://www.shell.com/about-us/major-projects/pearl-gtl.html]. An economical, efficient and productive process for producing gasoline and high octane fuels from NGL would reduce dependence on oil, lower fuel cost and be welcome by the industry. It is known that natural gas methane is converted to methanol via synthesis gas, CO & $H_2$. But, methanol addition to gasoline is very limited and does not produce a high quality fuel. An efficient process to convert methanol to propanol and pentanol would be welcome by the industry.

SUMMARY OF THE INVENTION

The present invention relates to free radical reaction methods in which low molecular weight, C2 to C6, unsaturated organic compounds such as ethylene and/or propylene are reacted with low molecular weight, C1 to C15, preferably C1 to C10 saturated organic compounds to form low molecular weight, linear or branched C3 to C24, preferably C3 to C12 organic compounds. For example, in some aspects the present invention provides improved strategies to carry out Equation (1) to produce a reaction product for which n is 1 or 2, preferably 1. In some aspects, as another example, the present invention also provides improved strategies for carrying out reactions according to Equation (2). When the unsaturated reactant includes an olefin and the chain transfer agent includes a hydrocarbon, one resultant low molecular weight product is a hydrocarbon alkylate with high octane number (defined below). In other aspects, the present invention provides strategies to react ethylene with C1 to C15 organic compounds in a manner to provide C3 to C24 products in which the ethylene is added to the C1 to C15 reactant as a linear chain. The resultant substantially linear products are useful in the formulation of diesel fuel. When the chain transfer agent includes an alcohol, the resultant product includes an alcohol whose molecular weight is increased by the addition of one or two, preferably one, residues of the unsaturated reactant to the chain transfer agent. The present invention is able to produce an improved yield of products relative to the amount of initiator as compared to many conventional processes.

Although the present invention can be practiced with a wide range of C1 to C15, preferably C1 to C10 saturated organic compounds, the type of product(s) desired impacts the choice of which C1 to C15 or C1 to C10 reactant(s) to use. For example, C1 to C10 alcohols can be reacted with unsaturated co-reactants to produce linear or branched C3 to C12 alcohols in which the number of carbon atoms of the starting C1 to C10 alcohol is increased by the number of carbon atoms in the unsaturated reactant. For example, reacting n-butanol (C4) with ethylene (C2) provides a C6 alcohol. Many of these alcohol products have high octane number, making them suitable as fuel additives to boost octane. If it is desired to prepare branched hydrocarbon products with high octane number, then it is desirable to select C3 to C10 hydrocarbons as the saturated organic compound. The C3 to C10 hydrocarbons can form secondary or tertiary radicals, which leads to desirable branching upon addition of the unsaturated reactant.

In some aspects, accordingly, the present invention provides free radical chemistry that allows branched, C5 to C12 organic compounds to be more easily and efficiently prepared from lower molecular weight starting materials. Branched products can be prepared even if all of the starting materials are linear. Branching occurs because the present invention is able to create secondary and tertiary carbon radicals with a more favorable ability to react with unsaturated co-reactants to increase molecular weight. In practical effect, a "branch" corresponding to a residue of the unsaturated species is added to such a secondary or tertiary site. When using C2 to C6 olefins and C3 to C10 reactants, highly branched C5 to C12 hydrocarbon alkylates are produced that are particularly useful to help provide fuels with high octane ratings. Therefore, the branched products can be used as high octane fuels or as fuel additives to boost octane of motor fuels.

In some embodiments, the present invention is useful to prepare low molecular weight, linear C3 to C12, preferably C3 to C5 alcohols from inexpensive starting materials such as ethylene and propylene on the one hand, and methanol or ethanol on the other hand. Generally, linear products result when the unsaturated reactant includes 2 or 3 carbon atoms and the chain transfer agent includes 1 or 2 carbon atoms. For example, ethylene addition to methanol according to the present invention provides an economical and efficient way to produce highly desirable n-propanol, which can be more difficult and more expensive to prepare using conventional strategies. Similarly, the present invention can react ethylene with ethanol to produce highly desirable 2-butanol. Similar reactions between propylene and methanol or ethanol can be used to prepare n-butanol and 2-pentanol, respectively, or even higher alcohols.

In some embodiments, the present invention is useful to prepare low molecular weight, substantially linear C6 to C24 hydrocarbons from inexpensive starting materials such as ethylene on the one hand and a C1 to C15 organic compound. Even if the initial ethylene is added onto the co-reactant at a secondary or tertiary radical site to provide an initial branch, the present invention teaches how to select reaction conditions so that additional ethylene residues are added in a linear fashion onto the initial ethylene residue. This aspect provides C6 to C24 products that are linear or substantially linear and that are useful in diesel fuel formulations.

The present invention is based at least in part upon the concept of carrying out the free radical reaction in the presence of atypically low concentrations of the unsaturated reactant(s). By doing this, chain transfer mechanisms are more favored while chain extension mechanisms are less favored. In some embodiments, principles of the present invention are helpful to create conditions under which chain transfer to form more stable, secondary or tertiary branched radicals is favored over olefin addition via chain extension, yet olefin concentration is sufficient to sustain the process. The result is an improved ability to form lower molecular weight, C5 to C12, highly branched products with greater ease and lower cost. This can be done with very low amounts of initiator material relative to the amount of products that are produced. The undue use of corrosive and hazardous materials such as HF and sulfuric acid can be avoided if desired.

In one aspect, the present invention relates to a method of making one or more C3 to C24, preferably C3 to C12 organic compounds, comprising the step of free radically reacting reactants comprising reacting at least one C2 to C6, unsaturated organic compound and at least one C1 to C15, preferably C1 to C10 chain transfer agent in a reaction zone in the presence of at least one free radical initiator under conditions effective to form a reaction product comprising at least one C3 to C24, preferably at least one C3 to C12 product, wherein the concentration of the at least one C2 to C6, unsaturated organic compound in the reaction zone is 3 weight percent or less based on the total weight of the at least one C2 to C6, unsaturated organic compound and the at least one chain transfer agent in the reaction zone.

In another aspect, the present invention relates to a method of making one or more C5 to C12 hydrocarbon compounds, comprising the step of free radically reacting reactants comprising reacting at least one C2 to C6 olefin and at least one C3 to C10 hydrocarbon in a reaction zone in the presence of at least one free radical initiator under conditions effective to form a reaction product comprising at least one branched, C5 to C12 hydrocarbon product, wherein the concentration of the at least one C2 to C6 olefin in the reaction zone is 3 weight percent or less based on the total weight of the at least one C2 to C6 olefin and the at least one C3 to C10 hydrocarbon in the reaction zone.

In another aspect, the present invention relates to a method of forming an alcohol, comprising the step of free radically reacting reactants comprising at least one C2 to C6 olefin and at least one saturated, C1 to C10 alcohol in a reaction zone in the presence of a free radical initiator under conditions effective to form a reaction product comprising at least one C3 to C12 alcohol, wherein the concentration of the at least C2 to C6 olefin the reaction zone is 3 weight percent or less based on the total weight of the at least one C2 to C6 olefin and the at least one saturated, C1 to C10 alcohol in the reaction zone.

In another aspect, the present invention relates to a method of making a fuel, comprising the steps of:
  free radically reacting reactants comprising at least one C2 to C6, unsaturated organic compound and at least one C1 to C10 chain transfer agent in a reaction zone in the presence of a free radical initiator under conditions effective to form a reaction product comprising at least one C3 to C12 product, wherein the concentration of the at least one C2 to C6, unsaturated organic compound in the reaction zone is 3 weight percent or less based on the total weight of the at least one C2 to C6, unsaturated organic compound and the at least one C1 to C10 chain transfer agent in the reaction zone; and
  incorporating the at least C3 to C12 product into a fuel composition.

In another aspect, the present invention relates to a method of making a fuel, comprising the steps of:
  free radically reacting reactants comprising at least one C2 to C6 olefin and at least one saturated, C3 to C10 hydrocarbon in a reaction zone in the presence of a free radical initiator under conditions effective to form a reaction product comprising at least one branched C5 to C12 hydrocarbon product, wherein the concentration of the at least C2 to C6 olefin in the reaction zone is 3 weight percent or less based on the total weight of the at least one C2 to C6 olefin and the at least one saturated, C1 to C10 hydrocarbon in the reaction zone; and incorporating the at least one branched C5 to C12 hydrocarbon compound into a fuel composition.

In order to help favor the formation of one or more branched C5 to C12 products in any aspects of the present invention, at least one chain transfer agent includes 3 to 10 carbon atoms even when using linear starting materials. These species can form secondary or tertiary radicals, and the practice of the present invention favors the addition of the unsaturated reactant to these secondary or tertiary radicals to form desirable branched products. Such addition is much less favored in many conventional practices or may involve much more extensive use of hazardous or corrosive materials to facilitate the reaction.

DETAILED DESCRIPTION

The present invention will now be further described with reference to the following illustrative embodiments. The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

All percentages and amounts of materials (e.g. ppm) are on a weight basis unless otherwise expressly stated. As used herein, a "major portion" refers to a portion that is at least 50 weight percent, more preferably at least 75 weight percent of the products have the characteristic based upon the total weight of the product compounds.

In some aspects, the present invention provides methods and systems to prepare linear or branched C3 to C24, preferably C3 to C12, or even C5 to C12 organic compounds from reactants including one or more unsaturated, C2 to C6 organic compounds ("unsaturated reactant") and one or more C1 to C15, preferably C1 to C10, or even C3 to C10 chain transfer agents. In practical effect, the present invention reacts one or more unsaturated organic compounds and one or more saturated, C1 to C15, preferably C1 to C10, or even C3 to C10 compounds (preferably aliphatic compounds) under conditions effective to form higher molecular weight, C3 to C24, preferably C3 to C12, or even C5 to C12, linear or branched products. Preferred reactants in this aspect include one or more C2 to C6 olefins and one or more C1 to C15, preferably C3 to C10 hydrocarbons to provide preferred products in the form of C3 to C24, preferably C3 to C12, or even C5 to C12, branched hydrocarbons. The reaction product tends to be a mixture that includes low molecular weight compounds incorporating one to two moles of residues of the unsaturated reactant per one mole of the chain transfer agent(s). The resulting branched compounds may have high octane number, making them useful as high octane fuels or as additives to boost the octane rating of motor fuels.

In other aspects, the present invention provides methods and systems to prepare branched or linear C3 to C12 organic compounds from reactants including one or more unsaturated, C2 to C6 organic compounds ("unsaturated reactant") and one or more C1 to C10 chain transfer agents. Preferred reactants include one or more C2 to C6 olefins and one or more C1 to C10 alcohols to provide preferred products in the form of C3 to C12 alcohols. This aspect of the invention provides an excellent strategy to controllably increase the molecular weight of a starting alcohol such that the number of carbon atoms of the starting C1 to C10 alcohol is increased by the number of carbon atoms in the unsaturated reactant. For example, methanol (C1) can be reacted with ethylene (C2) to prepare a C3 alcohol or with propylene (C3) to prepare a C4 alcohol. The ability to prepare alcohols such as propanol so easily from readily available starting materials is a significant advantage, because propanol is in high demand and is more difficult to make using many other conventional processes. When using methanol as a reactant, all or a portion of the methanol may be made from methane via a suitable source such as synthesis gas or natural gas.

Some low molecular weight compounds (e.g., isobutane) have high octane number but are more volatile than might be desired for use in a motor fuel. Advantageously, representative modes of practice can implement controlled addition of unsaturated reactants to these molecules to thereby transform them into high octane compounds with slightly higher molecular weight, but lower volatility. The result is that the transformed compounds, due to their high octane number and lower volatility, can be used more extensively as a fuel or fuel additive.

When both the unsaturated reactant and chain transfer agent reactants include hydrocarbons (defined below), the practice of transforming lower molecular weight hydrocarbons into higher molecular weight hydrocarbons with high octane rating (defined below) is referred to as alkylation. Additionally, the high octane products are referred to as alkylates. Alkylates are a desirable class of additives to boost octane, because other additives such as toluene or ethanol are more toxic than desired, phase separate in fuel mixtures, or boost octane at the expense of fuel quality.

In the practice of the present invention, the octane rating is given by the Research Octane Number (RON). Generally higher octane fuels with higher octane numbers are desirable to provide more control of fuel combustion in motor fuel engines. For example, boosting octane can help reduce engine knocking that otherwise could lead to excessive engine wear or damage.

Importantly, the present invention is able to practice alkylation without requiring the use of HF or $H_2SO_4$ catalysts. This makes the practice of the present invention less costly, safer, and more environmentally friendly to practice as compared to conventional processes that must use HF or $H_2SO_4$ acid catalysts.

The compounds prepared in the practice of the present invention can be used in diesel fuel formulations, as high octane fuels or as additives to boost octane in a wide range of motor fuels for motor-driven equipment such as automobiles, trucks, marine vessels, aircraft, rockets, generators, pumps, garden machinery, motorcycles, other equipment, and the like. Accordingly, one or more compounds prepared in the practice of the present invention may be incorporated into a fuel composition in a manner effective to constitute from 0.01 weight percent to 100 weight percent, preferably 0.5 weight percent to 100 weight percent, more preferably 5 weight percent to 100 weight percent of a fuel composition. A fuel is any composition that can be made to react with other substances, such as being controllably combusted in the presence of oxygen, so that it releases energy on demand as heat energy or to be used for work. A motor fuel is a fuel that is used to provide power to motor-driven equipment. Fuels can be solids, liquids, and/or gases. Fuels may be derived in whole or in part from fossil fuels (e.g., crude oil, shale oil, natural gas, etc.), biomass, chemical synthesis, combinations of these, and the like.

Product mixtures of the present invention desirably provide one or more desired products but also may include one or more lighter species (e.g., unreacted reactant(s)) as well as some heavier oligomeric product species. In some applications, such product mixtures may be further processed if desired to purify the C3 to C12 content. For example, consider an example in which C3 to C12 species are the desired products. Resultant product compositions may be purified so that the one or more of such C3 to C12 species constitute 50 weight percent to 100 weight percent, preferably 70 weight percent to 100 weight percent, more preferably 90 weight percent to 100 weight percent of the composition based on the total weight of carbon and hydrogen containing species in the composition. For some fuel applications, it may be the case that C5 to C8 species are the most desirable to use as fuel or fuel additives. Accordingly, the product compositions may be purified so that one or more C5 to C8 species constitute 50 weight percent to 100 weight percent, preferably 70 weight percent to 100 weight percent, more preferably 90 weight percent to 100 weight percent of the composition based on the total weight of carbon and hydrogen containing species in the composition. In diesel fuel applications, it may be the case that the C6 to C24 species are the most desirable. Accordingly, the product composition may be purified so that the C5 to C24 species constitute 50 weight percent to 100 weight percent, preferably 70 weight percent to 100 weight percent, more preferably 90 weight percent to 100 weight percent of the composition based on the total weight of carbon and hydrogen containing species in the composition.

The practice of the present invention not only can be used to prepare additives to boost octane rating in fuels derived from crude oil, but it also helps to provide a more economical and efficient way to produce high octane gasoline and other high octane fuels from chemical synthesis, natural gas and/or biomass sources. Importantly, the additives of the present invention can be blended into suitable natural gas liquid mixtures or biomass mixtures, e.g., those preferably processed to include a major portion of one or more C4 to C12, preferably one or more C6 to C8 hydrocarbons, to prepare gasoline. The principles of the present invention offer the potential to derive fuel from natural gas or biomass sources in a way that is more economical and more efficient than a practice such as the "Fischer-Tropsch" synthesis. For example, the present invention can be used to prepare gasoline grade hydrocarbon mixtures from natural gas liquids and ethylene/ethane mixtures, wherein the ethylene/ethane mixtures may also be derived from raw natural gas sources.

The present invention is versatile and can use linear, branched, and/or cyclic reactants. As an advantage, the present invention is able to prepare linear or branched hydrocarbon reaction products and linear or branched alcohol reaction products even when starting from linear reactants. As described below, and without wishing to be bound by theory, it is believed that this capability results because the present invention allows a meaningful degree of chain transfer steps to occur in free radical reaction chain reaction steps. The ability to promote chain transfer is believed to allow secondary and tertiary radicals to form, which then lead to branched products by addition of unsaturated compounds to these radicals. This is in contrast to reaction strategies that would tend to favor too much chain extension, as chain extension tends to favor the production of primary radicals and correspondingly larger, linear reaction products.

As used herein, an "organic compound" refers to a compound that includes at least one carbon atom, at least one hydrogen atom, and optionally one or more other types of atoms. For instance, an organic compound may include at least one carbon atom, at least one hydrogen atom, and optionally at least one heteroatom selected from N, O, S, P, and combinations of these. Some organic compounds may be linear, branched, or cyclic. Some organic compounds may be aliphatic or aromatic. Some organic compounds may be saturated or unsaturated. Some organic compounds may be solids, liquids, gases, or plasmas, and may be amorphous or crystalline. Some organic compounds may be salts (ionic) or nonionic. Some organic compounds may be substituted or unsubstituted. Embodiments with more than one cyclic moiety may include one or more bridges, two or more rings that are fused, and/or two or more rings that are linked by single bonds or linking groups. Some organic compounds may include spiro carbon atoms.

Hydrocarbon(s) may be used as chain transfer agent(s) or unsaturated reactant(s). As used herein, a "hydrocarbon" is an organic compound formed entirely from hydrogen and carbon atoms. Hydrocarbons include alkanes, alkenes, alkynes, and aromatic compounds. Hydrocarbons may be linear, branched, and/or cyclic.

An organic compound such as a hydrocarbon or group of hydrocarbons may be referred to by the designation C(N), Where C is a symbol representing carbon and (N) is a number indicating the number of carbon atoms in the hydrocarbon or group of hydrocarbons. For example, C1 refers to methane, the smallest hydrocarbon having one carbon atom. C2 refers to hydrocarbons with 2 carbon atoms such as ethane, ethene, and ethyne. C3 refers to hydrocarbons with 3 carbon atoms, etc. Polymeric hydrocarbons such polyethylene, polypropylene, polystyrene, ultrahigh molecular weight polyethylene, and the like may have large (N) values including but not limited to (N) values in the range from 50 to 100,000 or even higher. This designation approach also may be used to refer to hydrocarbons having carbon atoms in a range. For example, the designations C1-4 or C1 to C4 both refer to the group of hydrocarbons having from 1 to 4 carbon atoms. As another example, the designation C(N)+ refers to hydrocarbons having N or more carbon atoms. According to this kind of designation, C3+ refers to hydrocarbons having 3 or more carbon atoms.

A "chain transfer agent" includes any saturated organic compound including a free radically reactive C—H bond that is able to form a primary, secondary, or tertiary radical in the presence of an unsaturated organic compound and an initiator. Exemplary C—H bonds of a chain transfer agent have bond dissociation energy in the range from 84 kcal/mole to 98 kcal/mole as reported in reported in Yu-Ran Lo, *Handbook of Bond Dissociation Energies in Organic Compounds*, CRC Press; 1 edition (Dec. 26, 2002). In the practice of the present invention, if the actual bond dissociation energy is not available from this source, then a saturated organic compound having a C—H bond is deemed to be a chain transfer agent if, using the procedure of Example 3 below, the reaction of that compound with ethylene produces one or more, higher molecular weight, branched C4 to C12 products that are the result of addition of at least one residue of ethylene to a unit that is a residue of the compound.

One commercially important practice involves separating natural gas into one or more light hydrocarbon components and one or more heavy hydrocarbon components respectively. As used herein, the term "light" with respect to a hydrocarbon processing refers to a component (which may be a batch or stream) that contains an enriched C1 and/or C2 hydrocarbon content and that was obtained from a hydrocarbon feed mixture comprising C1 and/or C2 hydrocarbons as well as one or more C3+ hydrocarbons. The term "heavy" with respect to hydrocarbon processing refers to a component that comprises one or more enriched C3+ hydrocarbons and that was obtained from a hydrocarbon feed mixture comprising C1 and/or C2 hydrocarbons as well as one or more C3+ hydrocarbons.

In the natural gas industry, the term "natural gas liquids" or "NGL" has been used to refer to the C2+ content of natural gas. This approach to defining NGL implies a separation between C1 on the one hand, and C2+ hydrocarbons on the other hand. Accordingly, in the practice of the present invention, the terms "natural gas liquids" or "NGL" or "heavy" shall refer to a heavy component comprising C2+ hydrocarbons that is separated from a hydrocarbon mixture comprising C1 and/or C2 hydrocarbons as well as one or more C3+ hydrocarbons. Advantageously, the present invention provides additives to help boost the octane rating of NGL material, making the material more suitable for use as a fuel, particularly a motor fuel. The present invention also is able to process the ethane component of natural gas to produce a stream containing ethylene and ethane and then to use that stream or a portion of the stream to prepare fuels or fuel additives. For example, the light stream can then be used as a source of ethylene to use as an unsaturated reactant in the reactions of the present invention. In the meantime, all or a portion of the heavy stream content of natural gas can be used as a chain transfer agent in the reactions of the present invention. Hence, as an option, one or both of the unsaturated reactant or chain transfer agent reactants used in the practice of the present invention can be sourced from natural gas.

The term "high octane" refers to an RON of at least 80, preferably at least 85, and more preferably at least 90. Some high octane fuels even may have a RON of 100 or more.

Hydrocarbons may be gases, liquids, or solids at standard temperature and pressure (referred to as "STP" conditions, which are 25° C. and 1 atm absolute). For example, methane, ethane and propane are gases at STP conditions. Hexane and benzene are examples of hydrocarbons that are liquids at STP conditions. Waxes (paraffin wax and naphthalene, for instance) and polymers such us polyethylene, polypropylene, and polystyrene are examples of hydrocarbons that are solids at STP conditions. Other hydrocarbons may be gases at STP conditions but may be pressurized to place these into liquid form.

In one aspect, the present invention provides a method of using at least one unsaturated reactant and at least one chain transfer agent to prepare a product that includes one or more higher molecular weight compounds for which the increase in molecular weight is limited. Preferred modes of practice improve the production of product compounds in which 1 to 10, preferably 1 to 6, more preferably one or two, or even more preferably one residue of an unsaturated compound is added to a residue of a chain transfer agent. A preferred mode of practice involves using one or more C2 to C6 hydrocarbon unsaturated reactants and one or more C1 to C15, preferably C1 to C10, or even C3 to C10 hydrocarbon chain transfer agents to prepare a product comprising one or more linear or branched hydrocarbon products C3 to C24 products such as C5 to C12 hydrocarbons with high octane number.

The present invention can be used to react unsaturated reactant(s) with chain transfer agent(s) according to Equation (1) and/or Equation (2):

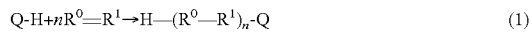

$$Q\text{-}H + nR^0{=}R^1 \rightarrow H\text{-}(R^0{-}R^1)_n\text{-}Q \qquad (1)$$

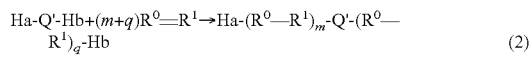

$$Ha\text{-}Q'\text{-}Hb + (m+q)R^0{=}R^1 \rightarrow Ha\text{-}(R^0{-}R^1)_m\text{-}Q'\text{-}(R^0{-}R^1)_q\text{-}Hb \qquad (2)$$

wherein for Equation (1): Q represents an organic moiety; the single bond(s) between the Q and H in the Q-H bonds has a bond dissociation energy often in the range from 84 kcal/mol to 98 kcal/mole, each of $R^0$ and $R^1$ independently is an organic moiety, $R^0$ and $R^1$ in $R^0{=}R^1$ are linked by a carbon-carbon double bond (e.g., ethylene, propylene, and other olefins in many instances); and —$(R^0{-}R^1)$— schematically represents a divalent organic moiety (e.g., a hydrocarbon alkylene moiety when $R^0{=}R^1$ is an olefin or mixture of olefins such as ethylene, propylene, and/or other olefins) corresponding to $R^0{=}R^1$; n is 1 or more, preferably 1 or 2, more preferably 1. In Equation (2), Q' is an organic moiety; each Ha and Hb is a different hydrogen atom; each Q'-Ha and Q'-Hb bond has a bond dissociation energy often in the range from 84 kcal/mol to 98 kcal/mole; $R^0$, $R^1$, $R^0{=}R^1$, and —$(R^0{-}R^1)$— are as defined above; and each of m and q independently is 0, 1 or 2, preferably 0 or 1 with the proviso that at least one of m and q is not 0 and the proviso that Ha and Hb are not attached to the same carbon. In preferred embodiments, at least one Q'-Ha or Q'-Hb bond involves the H (e.g., Ha and/or Hb) being bonded with a secondary or tertiary carbon atom.

Useful unsaturated reactants in the present invention include one or more unsaturated organic compounds, preferably one or more olefins (unsaturated hydrocarbons also referred to as alkenes) having one or more carbon-carbon double bonds, even more preferably one or more C2 to C6 olefins having one or more carbon-carbon double bonds. Examples of useful olefins include ethylene; propylene; linear or branched butene; linear, branched or cyclic pentene; linear, branched or cyclic hexene; or combinations of these. Preferred olefins are C2 to C5 olefins, more desirable C2 to C4 olefins, and even more desirably ethylene.

A variety of different ethylene feedstocks may be used in the free radical reaction in which the purity of ethylene in the feedstock may be selected from a wide range of purities. For example, in some modes of practice, the ethylene may be supplied in a relatively pure form in which the feedstock comprising ethylene includes at least 85 weight percent, preferably at least 90 weight percent, more preferably at least 95 weight percent, and even more preferably substantially 100 weight percent ethylene based on the total weight of the feedstock.

In other modes of practice, feedstock mixtures containing a lesser weight percent of ethylene may be used. For example, a substantial amount of commercially available ethylene is derived from feedstocks that, by their nature, contain both ethane and ethylene and thus are dilute in ethylene. In some instances, such feedstocks result from processes in which the nature of the chemistry causes the feedstock to include no more than about 80 weight percent ethylene based on the total weight of the feedstock. In many instances, such feedstocks may include from about 25 weight percent to about 80 weight percent ethylene based upon the total weight of the feedstock. Because ethane is substantially much less reactive and possibly substantially inert under reaction conditions used in many modes of practice, such feedstock mixtures may be used as is to carry out free radical reactions of the present invention. Alternatively, such mixtures may be purified or partially purified to provide a feedstock that is richer in ethylene, and such purified feedstock could then be used in the practice of the present invention. It is advantageous to feed the ethylene as a mixture with its parent saturated hydrocarbon, ethane to avoid the high cost of separating ethylene from ethane. The process efficiently reacts the chain transfer agent with the ethylene without significant impact to the starting ethane. It may be desirable to limit the presence of ethane to avoid undue pressure build-up in a reactor vessel, particularly if a vessel is not vented The ability to use a variety of widely available ethylene feedstocks is a practical advantage. At the same time there is a shortage of C3 to C24 alcohols, hydrocarbons and oxygenated chemicals (e.g., ketones, aldehydes, esters, ethers, etc.). The present invention fills the important need of using widely available feed materials to produce such products in high demand, selectively, and at lower cost. This fulfills a strong need for a selective, low capital process to produce low molecular weight C3 to C12 alcohols, or even C3 to C8 alcohols, or even C3 to C5 alcohols in illustrative modes of practice.

The chain transfer agent(s) used in the free radical reaction are any C1 to C15, preferably C1 to C10, saturated organic compounds that contain 1 (C1) to 15 (C15), preferably 1 (C1) to 10 (C10) carbon atoms and at least one free radically reactive C—H bond. Illustrative chain transfer agents are linear, branched, or cyclic organic compounds that are aliphatic. The illustrative chain transfer agents may be hydrocarbons or may be organic compounds including substituents such as one or more heteroatoms (e.g., one or more of O, S, P, N, combinations of these, or the like).

It can be appreciated, therefore, that a wide variety of aliphatic, saturated compounds having 1 to 15, preferably 1 to 10, or even 1 to 8 carbon atoms may be used as chain transfer agents in the practice of the present invention. Examples include alkanes (hydrocarbons), alcohols, ketones, aldehydes, esters, carboxylic acids, anhydrides, ethers, combinations of these, and the like. Some chain transfer agents may comprise only a single functionality or a combination of functionalities. For example, some chain transfer agents may be diols or triols or other compounds including a plurality of hydroxyl groups. Other multifunctional chain transfer agents may include at least one ether functionality and at least one alcohol functionality. Other multifunctional chain transfer agents may include at least one ester functionality and at least one hydroxyl functionality.

In some modes of practice, the chain transfer agent comprises one or more linear, branched, or cyclic C1 to C15, preferably C2 to C10 alkanes. Examples include ethane, propane, n-butane, i-butane, pentane, isopentane, combinations of these, and the like.

In some modes of practice, the chain transfer agent comprises one or more alcohols of the formula H—R—(OH)$_n$, wherein R is a hydrocarbylene moiety comprising 1 to 15, preferably 1 to 10 carbon atoms. The hydroxyl groups may be primary, secondary, or tertiary. Alcohols can be reacted with ethylene via free radical reactions to prepare products of the formula H—(CH$_2$CH$_2$)$_n$—ROH, wherein a major portion of the products have an n value of 1 or 2, preferably 1. Examples of suitable alcohols include methanol, ethanol, isopropanol, n-butanol, 2-butanol, isobutanol, ethylene glycol, neopentyl glycol, propylene glycol, glycerol, other C3 to C8 alcohols, combinations of these, and the like.

Illustrative examples of suitable ketones useful as a chain transfer agent include acetone, 2-butanone, other C4 to C12 ketones combinations of these, and the like.

Illustrative examples of aldehydes useful as a chain transfer agent include acetaldehyde, propionaldehyde, butyraldehyde, pentanal combinations of these, and the like.

Illustrative examples of ethers useful as a chain transfer agent include ethyl ether, isopropyl ether, butyl ether, tetrahydrofuran combinations of these, and the like.

Illustrative examples of carboxylic acids and anhydrides useful as a chain transfer agent include formic acid, acetic acid, propionic acid, succinic acid, succinic anhydride, maleic anhydride, isobutyric acid combinations of these, and the like.

Illustrative examples of alkanes useful as a chain transfer agent include propane, butane, isobutane, pentane, 2-methyl butane, toluene and other C4 to C12 alkanes combinations of these and the like.

Illustrative examples of esters useful as a chain transfer agent include methyl acetate, methyl propionate, ethyl acetate, methyl benzoate, propyl propionate, butyl propionate, ethyl 3-ethoxypropionate, combinations of these, and the like.

In some embodiments, a chain transfer agent used in the practice of the present invention comprises at least one C—H bond having a bond dissociation energy of less than 98 kcal/mole. In many such embodiments, the bond dissociation energy is greater than 84 kcal/mole. Such bond dissociation energies generally mean that chain transfer is exothermic. However chain extension is also exothermic. The present invention provides reaction conditions that favor chain transfer over olefin addition to help improve the ability to provide products of limited molecular weight. To help control the associated exotherm and to limit molecular weight build up, the present invention provides a high ratio of chain transfer agent to unsaturated reactant in the reaction zone. A key aspect in some modes of practice is to allow the chain transfer agent to form primary, secondary or tertiary radicals and then to add a single unsaturated compound to those radicals. When the chain transfer agent is a C3 to C10 species, a secondary or tertiary radical is able to form, and addition of the unsaturated reactant to that forms a branched product. This approach selectively favors, for example, olefin addition to more stable secondary and tertiary radicals rather than olefin chain extension. Ethylene and propylene are preferred olefins, as these are available at low cost and react favorably in the practice of the present invention. Ethylene is more preferred as being more selective to react with secondary and tertiary radicals.

In chemistry, bond-dissociation energy (BDE) is a measure of the strength in a chemical bond. It is defined as the standard enthalpy change when a bond is cleaved by homolysis at a defined temperature. Bond disassociation energies vary to some degree with temperature, but are typically reported at 298° K or 25° C. The bond dissociation energy of C—H bonds tends to decrease with increasing substitution on the carbon. Thus, the BDE for a primary C—H bond in ethane is about 98 kcal/mole whereas the BDE for the tertiary C—H bond in (CH$_3$)$_3$—C—H is about 92 kcal/mole. Additionally, C—H bond disassociation energies on carbons containing a heteroatom, such as an oxygen of an alcohol, tend to be lower than similar C—H bonds on carbons without a heteroatom. The corresponding radicals of carbon atoms bearing a heteroatom tend to be more stable, and olefin additions tend to add selectively at those sites.

Exemplary bond dissociation energies are reported in the following Table 1:

TABLE 1

Bond Disassociation Energies (Kcal per mole)-All Thermal Homolytic Cleavage

| Compound | Structure | Bond dissociation energy, kcal/mole, 25 C. |
|---|---|---|
| Methane | CH$_3$—H | 104 |
| Ethane | CH$_3$CH$_2$—H | 98 |
| Propane | (CH$_3$)$_2$CH—H | 95 |
| Isobutane | (CH$_3$)$_3$C—H | 92 |

TABLE 1-continued

Bond Disassociation Energies (Kcal per mole)-All Thermal Homolytic Cleavage

| Compound | Structure | Bond dissociation energy, kcal/mole, 25 C. |
|---|---|---|
| Water | HO—H | 119 |
| Any alcohol O—H | RO—H | About 104 |
| Any aldehyde C—H | $CH_3C(O)$—H | About 86 |
| Methanol | H—$CH_2OH$ | 94 |
| Ethylene | $CH_2$=CH—H | 118 |
| Propylene | $CH_2$=$CHCH_2$—H | 89 |
| Ethanol | H—$CH(CH_3)OH$ | 93 |
| Isopropanol | H—$C(CH_3)_2OH$ | 91 |
| Hydrogen peroxide | $HO_2$—H | 51 |
| C4 peroxide | HO—$OC(CH_3)_3$ | 46 |
| C8 peroxide | $(CH_3)_3CO$— $OC(CH_3)_3$ | 38 |

Additionally, a benzylic C—H bond has a bond dissociation energy of 90 kcal/mol, which is suitable in the practice of the present invention. Additional modes of practice may use toluene (methyl benzene) as a chain transfer agent. Bond dissociation energies of many hydrogen bonds is reported in Yu-Ran Lo, Handbook of Bond Dissociation Energies in Organic Compounds, CRC Press; 1 edition (Dec. 26, 2002).

The one or more unsaturated reactants and the one or more chain transfer agents are reacted in a reaction zone under conditions effective to form a reaction product comprising at least one linear or branched C3 to C24, preferably C3 to C12, or even C5 to C12 hydrocarbon compound and/or one C3 to C12 linear alcohol. Exemplary conditions include reacting the unsaturated reactant and chain transfer agent reactants in the presence of one or more free radical initiators. Free radical initiators are well known in the field of free radical synthesis and are substances that can produce radical species to promote radical reactions. Illustrative examples are halogen molecules such as chlorine; azo compounds such as azobisisobutyronitrile and/or 1,1'-Azobis (cyclohexanecarbonitrile); and organic and inorganic peroxides such as di-tertiary butyl peroxide (DTBP), cumene hydroperoxide, paramenthane hydroperoxide, dicumyl peroxide, tertiary butyl hydroperoxide (TBHP), tertiary butyl peracetate, cyclohexanone peroxide, decanoyl peroxide, laurel peroxide, diisopropylperoxydicarbonate, and hydrogen peroxide. DTBP is preferred as having low induced decomposition. As a drawback, DTBP is relatively expensive. However, low amounts of free radical initiator(s) are used in the practice of the present invention so that the expense of DTBP may be an insignificant burden. TBHP also is preferred. Although more susceptible to induced composition as compared to DTBP, TBHP is much less expensive. Also, initiator(s) may be used in such low amounts in the practice of the present invention such that the risks associated with induced decomposition are reduced.

The molar ratio of the total amount of unsaturated reactant material to the total moles of one or more free radical initiators as supplied to the reaction is 8:1 or more, preferably 20:1 or more, more preferably 40:1 or more, or even 80:1 or more. In many embodiments, such molar ratio is no more than 5000:1, preferably no more than 2000:1. This means that relatively little amounts of the free radical initiator(s) are present. This is an important aspect of the invention that is helpful so that the reaction results in products incorporating from 1 to 10, preferably 1 to 6, more preferably 1 to 3, even more preferably 1 to 2, even more preferably 1 alkylene residue(s) derived from unsaturated reactants.

Particularly because chain extension is so limited, the fact that so little initiator can produce such high levels of products is surprising and results at least in part by maintaining reaction conditions that favor chain transfer. In general, increasing the molar ratio of unsaturated reactant(s) to the initiator(s) and running the reaction continuously at high rate tends to produce a product mixture in which the average number of alkylene residues derived from unsaturated reactants is smaller. This is highly desirable when lower molecular weight products are more desired.

Even though the amount of initiator used in the practice of the present invention is relatively low, the methods of the present invention still produce a substantial amount of products per gram of initiator(s). For example, illustrative modes of practice may produce 100 grams or more of products per 1 gram (g) of initiator.

The ability of the present methods to produce so much product per gram of initiator is counterintuitive. Because initiator(s) are present in such low amounts, the initiators produce low concentrations of radicals in the reaction medium. Conventionally, an expectation would be that a low amount of desired product would result. Without wishing to be bound by theory, a rationale to explain the high production of product can be suggested. It is believed that the limited amount of unsaturated reactant (e.g., ethylene) to the chain transfer agent (e.g., alcohol), the limited amount of the initiator relative to the unsaturated reactant and running the reaction continuously at high rate produces a reaction environment in which chain transfer steps are favored. As a result, the methods of the present invention are able to provide branched products, whereas greater amounts of linear, higher molecular weight products results when chain transfer is less favored.

The reaction between the unsaturated reactant and chain transfer agent reactants is carried out such that the chain transfer agent is present in the reaction zone in a large stoichiometric excess relative to the unsaturated reactant. In particular, the concentration of the at least one unsaturated reactant in the reaction zone is 3 weight percent or less, preferably 2 weight percent, or even less than 1.0 weight percent or less based on the total weight of the at least one unsaturated reactant and the at least one chain transfer agent in the reaction zone. Desirably, the unsaturated reactant is present in an amount of at least at least 10 ppm, or even at least 100 ppm or even at least 500 ppm on a weight basis based on the total amount of unsaturated and saturated reactants in the reaction zone.

A preferred range for preparing branched products is 100 ppm to 1.2 weight percent, more preferably 100 ppm to 1.0 weight percent, even more preferably 200 ppm to 0.6 weight percent of the at least one unsaturated reactant based on the total weight of the at least one unsaturated reactant and the at least one chain transfer agent in the reaction zone. A preferred range for preparing products in which ethylene residues are added linearly unto the chain transfer agent(s) is 1.2 weight percent to 3 weight percent, more preferably 1.3 weight percent to 2.5 weight percent, even more preferably 1.4 weight percent to 2.2 weight percent of the at least one unsaturated reactant based on the total weight of the at least one unsaturated reactant and the at least one chain transfer agent in the reaction zone. These preferred ranges are particularly suitable when the unsaturated reactant comprises an olefin such as ethylene and/or propylene, preferably ethylene.

In the practice of the present invention, unless otherwise expressly stated, the values for ppm or weight percent are on a weight basis and are based on the total amount of unsaturated and saturated reactants in the reaction zone. In one mode of practice using 1 weight percent of unsaturated reactant based on the total weight of unsaturated reactant and chain transfer agent material was found to be suitable.

It has surprisingly been found that effective, efficient free radical initiated (catalyzed) reaction of unsaturated reactant with chain transfer agents can be to form a significant amount of low molecular weight, branched products (e.g., such as those resulting with incorporation of 1 or 2 moles of olefin per mole of hydrocarbon or oxygen containing hydrocarbon) when the concentration of unsaturated reactant in the reactor zone is atypically low.

Without wishing to be bound by theory, it is believed that the ability of the present invention to produce branched products without using HF or sulfuric acid catalysts relates to the nature of chain transfer and chain extension phenomena characteristic of free radical reactions. As an example, chain extension occurs when an olefin adds to a radical. Adding ethylene by chain extension is energetically favorable and has low activation energy. There is little barrier to this kind of reaction happening. Chain extension tends to build longer, linear, higher molecular weight molecules.

Chain transfer results when a new radical is created from a different radical. In practical effect, a proton (hydrogen) is transferred from a compound that becomes the new radical to the prior radical. Chain transfer tends to build more branched products. There is a higher barrier for chain transfer to occur than for chain extension.

It has surprisingly now been found that limiting the amount of the one or more unsaturated reactants in the reaction zone not only helps to provide products of limited size (e.g., products with 3 to 24, preferably 1 to 15, more preferably 1 to 10 carbon atoms), but also that controlling the amount of the one or more unsaturated reactants within certain ranges helps to control the degree of branching in the resultant products. Generally, restricting the unsaturated content in the reaction zone to lower values (e.g., 100 ppm to 1.1 weight percent, more preferably 100 ppm to 0.8 weight percent, even more preferably 200 ppm to 0.5 weight percent of the at least one unsaturated reactant based on the total weight of the at least one unsaturated reactant and the at least one chain transfer agent in the reaction zone) helps to favor forming products with more branching. In other aspects, restricting the unsaturated content in the reaction zone to higher values (e.g., 1.2 weight percent to 3 weight percent, more preferably 1.5 weight percent to 3 weight percent, even more preferably 2.0 weight percent to 2.5 weight percent of the at least one unsaturated reactant based on the total weight of the at least one unsaturated reactant and the at least one chain transfer agent in the reaction zone) helps to favor forming products with more linear addition of ethylene residues.

The result is that the present invention provides strategies for the controlled net addition of 1 to 6 moles, preferably 1 to 2 moles, or even 1 mole of olefin per mole of saturated C1 to C15 organic compound, or even per mole of saturated C3 to C15 organic compound on a weight average basis. Moreover, the olefin concentration in the reaction zone can be controlled to define the linear or branching character of the resulting product mixture. For example, in the case of ethylene addition, concentration ranges can be selected to provide a more linear product that is more useful for diesel fuel applications. This leads to the ability to produce essentially linear C6 to C24 hydrocarbons and alcohols. In this case olefin addition is favored to some desired degree over chain transfer by maintaining a minimum concentration of olefin in the reaction zone.

Without wishing to be bound by theory, a rationale to explain the ability to control branching can be suggested. The following Table 2 shows calculated, relative secondary and tertiary C—H bond ratios for the reaction of ethylene and isopentane at various concentrations of ethylene. For purposes of the column titled "Predicted Chain Transfer to Olefin Addition Ratio", a chain transfer constant of 0.01 is used. This means that only 1 collision in a hundred would be effective.

TABLE 2

Secondary and Tertiary C—H Bond Ratios at Various Ethylene Concentrations in Isopentane

| Isopentane wt % | Ethylene wt % | Moles Isopentane | Moles Ethylene | Mole Ratio Isopentane/ Ethylene | Equivalent ratio tertiary C—H to ethylene | Equivalent ratio secondary C—Hs to ethylene | Total equivalent ratio of tertiary and secondary C—Hs to ethylene | Predicted Chain Transfer to Olefin Addition Ratio* |
|---|---|---|---|---|---|---|---|---|
| 72 | 28 | 1.00 | 1.00 | 1 | 1 | 2 | 3 | 0.03 |
| 97.2 | 2.8 | 1.35 | 0.10 | 13.5 | 13.5 | 27 | 40.5 | 0.4 |
| 99.7 | 0.28 | 1.38 | 0.01 | 138 | 138 | 276 | 414 | 4.1 |
| 99.9 | 0.028 | 1.39 | 0.001 | 1390 | 1390 | 2780 | 4170 | 42 |
| 99.9 | 0.0028 | 1.39 | 0.0001 | 13900 | 13900 | 27800 | 41700 | 417 |

Assumes Total 100 g of Isopentane and Ethylene in all cases.
*Assumes REFct = 0.01 REFoa Note this ratio is approximate and likely temperature dependent.

Table 2 assumes that the chain transfer constants for tertiary and secondary hydrogens are the same. However, tertiary hydrogen tends to be more efficient in chain transfer reactions than secondary hydrogens. In practice, this means that it is likely that chain transfer will preferentially occur at tertiary hydrogen sites as compared to secondary hydrogen sites. The predicted chain transfer to olefin addition ratio approaches 1.0 at approximately 1.1% ethylene concentration in the reaction zone. Note that at 2.8% ethylene concentration in the reaction zone, the table predicts that on average chain extension (olefin addition) is favored 2.5 to 1 over chain transfer. This would suggest that the average amount of chain extension can be controlled if the concentration of ethylene in the reaction zone is controlled in a narrow range.

Further it is known the chain transfer constant is dependent on temperature. That is the chain transfer constant will get larger as both the reactivity of the reacting radical increases and as temperature increases. Thus a primary radical such as $CH_3CH_2^*$ is more reactive than a secondary radical such as $(CH_3)_2CH^*$, which in turn is more reactive than a tertiary radical such as $(CH_3)_3C^*$. Conversely, oxygen radicals such as $(CH_3)_3O^*$ are more reactive than primary $C^*$ radicals. The calculated data in Table 2 suggests the average degree of olefin addition to chain transfer would be controlled by controlling the concentration of olefin in the reaction zone in a desired range to give a desired average molecular weight of product and a desired degree of branching.

Conveniently, since ethylene and propylene are gases at room temperature, the concentration of these in the reaction zone may be monitored (controlled) by direct measurement e.g., IR or control of its partial pressure at a given reaction temperature. Thus at a given reaction temperature and olefin reaction rate, olefin (preferably ethylene or propylene) can be supplied at the rate of being consumed. For propane or any other hydrocarbon instead of isopentane, extended olefin addition without chain transfer also should be controllable to a desired degree in a similar manner. It follows, therefore, by using higher yet limited concentrations of olefin, that linear addition of up to 5 to 10 moles of ethylene per mole of liquid hydrocarbon would be achievable before chain transfer in this case provide to linear products suitable diesel grade hydrocarbon fuel. Yet, using lower and limited concentrations of olefin could be practiced to favor branching.

The concept of favoring linear addition is illustrated below in Examples 1 and 2. The concept of favoring branching is illustrated below in the other examples. Example 1 was run at 300 psig partial pressure ethylene, and Example 2 run was run at 80 psig partial pressure ethylene. In Example 1, between 3 and 4 moles of ethylene was added mainly by linear addition per mole 2,3-dimethyl butane. In Example 2, a little over 2 moles of ethylene was added mainly by linear addition on average to 2,3-dimethyl butane. Note in Example 3 that the more branched product was almost exclusively resulting from addition of only one or two moles of ethylene per mole of hydrocarbon. Examples 1 to 3 were batch reactions. It is expected that in continuous reaction mode, the ethylene concentration (olefin) can be monitored (instrumentally, IR) and controlled in even a tighter range to yield even a more specific defined product mixture.

In contrast to the practice of the present invention, higher concentrations of olefin above 3 wt % leads to many chain extension steps, which in turn leads to more linear products with an undesirable wide product molecular weight distribution. In contrast, using lower concentration of unsaturated reactant in accordance with the present invention allows chain transfer to dominate. A possible reason for this is that with such a low unsaturated reactant content, the radical is more likely to encounter and react with chain transfer agent or another radical rather than another unsaturated reactant. In other words, chain transfer becomes more prominent because encounters and reaction with the sparsely present unsaturated reactant occur less frequently.

The increased prominence of chain transfer facilitates formation of the more stable secondary and tertiary free radicals. Generally speaking it is known that tertiary carbon radicals (those on a carbon with three other carbons attached) are more stable than secondary carbon radicals (those on a carbon with two other carbons attached) which in turn are more stable than primary carbon radicals (those on a carbon with only one other carbon directly attached). The less stable radicals are more reactive.

By way of example in the case of ethylene addition to any radical only primary radicals tend to be initially formed. It is energetically favorable for these primary radicals to undergo chain transfer to form more stable secondary or tertiary radicals. However, it is known that olefin addition occurs very readily and occurs more rapidly than chain transfer.

In the meantime, it has been reported that chain transfer efficiencies for C—H bonds can be in the $10^{-2}$ range (that is only one collision in 100 leads to effective H transfer). [Reference—"Free Radicals" Volume II Edited by Jay K. Kochi, 1973 or Reference 4—"Free Radical Telomerization" Edited by Charles Stark 1974]. The present invention appreciates that this observation means that it is desirable to maintain a high ratio of reactive C—H bonds relative to unsaturated reactant in the reaction zone to promote chain transfer (formation of more stable, branched, highly substituted radicals). At the same time it is important to have sufficient unsaturated reactant concentration in the reaction zone to sustain the catalytic nature of the process. Uniquely, the present invention teaches the ability to practice a unsaturated reactant reaction process at a concentration low enough to promote chain transfer yet be sufficient to sustain the catalytic process. An unexpected outcome is the chain transfer process leads to more highly branched or linear radicals on demand. In the case of branched radicals, these in turn lead to more highly branched, higher octane products. As a distinct advantage, the present invention is able to prepare branched, high octane compounds without having to use HF or sulfuric acid catalysts.

The reaction between the unsaturated reactant and chain transfer agent material may be carried out in batch or continuous fashion. Although the reaction can be carried out in batch or continuous modes, continuous modes are more preferred. In batch modes, the ratios of reactants and initiator(s) tend to change as the reaction proceeds. This can make it more difficult to control the nature (e.g., the n values) of the products produced by the reaction. In contrast, the ratios are much easier to control and maintain in continuous modes, making it easier to control the nature of the products.

In continuous modes, a feed mixture comprising the unsaturated reactant material, chain transfer agent material, and initiator material is feed to the reaction zone at the desired rates and ratios. When the feed includes ethylene derived from ethane, it may be economically advantageous to feed the ethylene as a mixture with its parent ethane as the ethane will not unduly interfere, if at all, with the desired reaction. The investment to separate the ethylene and ethane also is avoided. A similar, favorable feed strategy can be used to feed mixtures of propylene and propane when the propylene is derived from propane.

The chain transfer agent to unsaturated reactant feed weight ratio can be anywhere from 1:200 to 200:1. The total feed rate is adjusted so as to maintain the unsaturated reactant concentration at steady state in the reaction zone(s) at less than 3 wt % based on the total weight of the chain transfer agent and unsaturated reactant material in the reaction zone. Olefin concentrations, for example, can be monitored in the reaction zone in any number of phases by various methods known to those in the art, e.g. IR cells. This generally means the total unsaturated reactant feed rate is slightly less or equal to its consumption rate in the reaction zone. The total unsaturated reactant reaction rate is mainly dependent on its steady state concentration, the initiator (catalyst) chosen, the initiator feed rate, the capacity of the reactor and other process parameters, such as temperature and pressure. In this way product of desired (average) molecular weight and poly dispersity can be produced. A reaction system conducive to good mixing and free radical (catalytic) reaction processes is also preferred. As used herein, molecular weight for a product mixture is the weight average molecular weight unless otherwise expressly noted.

Note that the steady state weight ratio of chain transfer to unsaturated reactant agent in the reaction zone is higher than the feed weight ratio. This relationship is important in order for the reaction zone to favor chain transfer and thereby provide a reaction strategy that favors producing lower molecular weight, branched products. The steady state weight ratio in the reaction zone is higher than the feed weight ratio because the reaction is carried out such that the molar conversion of the unsaturated reactants to products desirably is greater than 40 molar percent, preferably at least 70 molar percent, and even more desirably at least 90 molar percent to substantially 100 molar percent. In the meantime, the reaction is carried out so that the molar conversion of the chain transfer agents to products is lower such as less than 60 molar percent, preferably less than 25 molar percent, or even less than 10 molar percent.

The conversion rates of the unsaturated reactant and chain transfer agent are controlled by adjusting one or more of the flow rate of the reactants, the temperature of the reaction zone, the pressure in the reaction zone, and/or the residence time in the reaction zone. For example, if conversion of the unsaturated reactant to products is too low, the temperature, pressure, flow rate, and/or residence time could be increased. The goal in many embodiments is to select these parameters in a manner effective to help ensure that unsaturated reactant conversion preferably is greater than 50% and more preferably greater than 80% at steady state conditions.

It can be appreciated that the weight ratio between the unsaturated reactant and chain transfer agent material in the feed is not critical and can be any suitable ratio. What is important is that the rate of the unsaturated reactant feed into the reaction zone is sufficiently low to keep the concentration of the unsaturated reactant in the reaction zone sufficiently low. This helps to ensure a high ratio of reactive C—H bonds on the chain transfer agent relative to the unsaturated reactant in order to favor chain transfer and the corresponding formation of branched products. Desirably, to help maintain low unsaturated reactant concentration in the reaction zone, the feed rate of the unsaturated reactant is less than or equal to the consumption rate of the unsaturated reactant in the reaction zone.

Even though it is desired that chain transfer dominate relative to olefin addition, the chain transfer desirably is not totally dominant or else only chain transfer agent radicals would combine to terminate the reaction, and this would severely limit yield per weight of initiator. At least some lower threshold of olefin is needed, therefore, so that some degree of chain extension occurs. In practical effect, the presence of some low, but threshold amount of the unsaturated reactant helps to assure that some significant degree of olefin addition occurs to provide the desired products. The presence of the low amount of unsaturated reactant helps to propagate the reaction in a favorable manner.

The present invention also includes the option to recycle of one or more product components. For example, if it is desired to produce mainly C8 to C12 branched compounds, these desired products can be recovered from the product stream with smaller products in the remainder stream recycled back to the reaction zone for re-processing.

The reaction may occur within a wide temperature range. If the temperature is too low, the reaction may take too long to proceed to the desired degree of conversion and/or selectivity. If the temperature is too hot, undue amounts of by-products may result and/or the risk of thermal degradation of reactants or products increases. Balancing such concerns, the reaction desirably occurs in the range from 30 C to 300 C, preferably 50° C. to 200° C. Optionally, the reaction may occur in one or more temperature stages. For example, an initial portion of the reaction may occur at a first temperature or temperature range such as at a temperature in the range from 70° C. to 170° C. Then, a subsequent portion of the reaction may occur at a second temperature or temperature range such as at a temperature in the range from 100° C. to 250° C.

The reaction may be carried out at one or more pressures selected from a wide range. If the pressure is too low, then it may be harder to keep ethylene in the reaction zone. If the pressure is too high, then reactor operation costs maybe high. As illustrative guidelines, the reaction may be carried out a pressure from 40 psig to 2400 psig, preferably 100 psig to 1500 psig. Higher pressures may be used, but offer little added benefit but involve more procedural and equipment expense. In some embodiments, it has been found that running at reaction pressures in the 200 psi to 1000 psi range and at temperatures 120° C. to 200° C. helps to ensure sufficient, but not excessive, ethylene availability and high chain transfer efficiency.

Generally, it is desirable to exclude oxygen from the reaction unless oxygen is being used to generate peroxide. Accordingly, it is desirable to carry out the reaction in the absence of a headspace or optionally in the presence of at least one inert gas such as $N_2$, He, Ar, $CO_2$, combinations of these, or the like. Optionally, the reactants and initiators may be de-gassed prior to use in the reaction. As a further option, the reactants and initiators may be dried prior to use in the reaction as well so that the ingredients as supplied to the reaction have a reduced moisture content of 0 weight percent to 1 weight percent, more preferably 0 weight percent to 0.1 weight percent based on the total weight of reactants and initiator.

The reaction may occur in a plurality of reaction zones. These may be arranged in parallel and/or in series. The feed to each reaction zone may be independently controlled. For example, olefin concentration may vary among multiple zones in order to adjust the product distribution of products produced from each zone. Optionally the olefin may be allowed to react to a very low concentration in one or more reaction zones if desired. Also as an option, the concentration of the olefin in any reaction zone(s) may be adjusted to one or more values within narrow or defined range(s) as a reaction proceeds in order to control the product mix. Generally, lower concentrations of the unsaturated reactant tend to provide product mixtures with a lower weight average molecular weight. Reducing the feed rate of the unsaturated reactant or allowing the concentration in the reactor to become more depleted are ways to reduce the steady state concentration. Conversely, increasing the feed rate of the unsaturated reactant is one way to increase the steady state concentration.

Metal materials include pure metals, metal alloys, intermetallic compositions, metal ions, some metal salts and the like. Metal materials can quench the desired reaction such as by promoting radical chain termination via a disproportionation reaction. Metals and metal salts are believed to do this by converting carbon radicals to positive ions via electron transfer processes. Metal oxides, carbides and nitrides incorporating easily oxidized or easily reduced metal constituents (e.g., transition metals such as Fe) also can quench the desired reaction via similar mechanisms. Examples of such compounds include ferric oxide, ferrous oxide, ferric chloride, combinations of these and the like. Accordingly it is desirable to minimize or even exclude metal materials and such transition metal oxides from the reaction zone in which the reaction is occurring as much as is practicable. It is particularly desirable to minimize or exclude metals, especially easily oxidized or easily reduced metal ions in the reaction zone in the practice of the present invention where the initiator is present at relatively low concentrations relative to the reactants.

Minimizing or excluding metals from the reaction zone can be accomplished in different ways. A first approach is to carry out the reaction in a reaction zone whose surfaces in contact with the reaction materials are substantially inert with respect to the reactants, reaction products, oxidation, reduction, and reaction by-products (if any). A wide range of such inert surfaces may be used. Examples of materials useful to form inert surfaces include fluoropolymers such as polytetrafluoroethylene (PTFE), glass such as quartz, glass and some ceramic materials such as oxides, nitrides, or carbides combinations of these and the like that contain minimal amounts, e.g., under 10 weight percent, preferably under 3 weight percent, more preferably under 0.5 weight percent of easily oxidized or reduced metals based on the total weight of the materials. Reactor vessels with PTFE walls or glass walls are preferred. PTFE is available under the trade designation TEFLON from E. I. Du Pont de Nemours.

Another approach to minimize contact between metal materials and the reaction medium is to carry out the reaction in a vessel whose reaction volume is sufficiently high so that the reaction volume is relatively large compared to the surface areas of the surfaces that define the reaction volume. This can be accomplished, for example, using reactor vessels (e.g., cylindrical reactors) with volumes of at least about 20 liters, more preferably at least about 400 liters or as high as several 100,000 liters. In illustrative embodiments, a vessel may be used in which the surface to volume ratio is less than 0.5 cm-1.

Another approach is to carry out the reaction under conditions such that the reaction proceeds to the desired degree of completion in a desired time frame that allows reaction rate to be less than mixing rate. This allows a feed to be adequately mixed into the reaction zone so that reactions occur in the presence of an appropriate dilution of olefin. Depending on the type of mixing used, a reaction may proceed to the desired degree of completion over a range of time periods, e.g., 1 to 60 minutes. The temperature can be adjusted to control the reaction rate. Generally, higher temperatures provide faster reaction rates. In some modes of practice, suitable reaction rates are accomplished by carrying out the reaction at higher temperatures, e.g., 140° C. to 200° C. Reactants can be separately pre-heated to near the desired reaction temperature before being combined to further help shorten residence time in the reactor. Alternative, the feed can be used to absorb some of the heat of reaction. The heat of reaction can desirably be balanced to match the feed rate.

The reaction may be conducted in one or more different phases such as in the gas, super critical, gel, or liquid phases. Although the reaction may be conducted in any phase or multiple phases, the liquid phase is preferred.

The reaction involving the C2 to C6 unsaturated organic compound and the C1 to C15, preferably C1 to C10, or even C3 to C10 saturated hydrocarbon compound is effective to form a product comprising one or more branched or linear C3 to C24, or even C5 to C12 hydrocarbons. Advantageously, the present invention provides an efficient process for producing C5 to C12 branched organic compounds by reacting an unsaturated C2 to C6 organic compound such as ethylene at low reaction zone steady state concentration with a C3 to C24, or even C3 to C10 saturated organic compound such as a hydrocarbon. The final product includes linear or branched compounds incorporating residues of 1 to 10, preferably one to two moles of the unsaturated reactant (e.g., olefin such as ethylene) per residue of one mole of the saturated reactant (e.g, saturated hydrocarbon and/or alcohol). More preferably the final product includes branched compounds that incorporate one mole of the unsaturated reactant per one mole of the saturated reactant.

In illustrative modes of practice, the present invention provides a controlled and efficient reaction of one or more low molecular weight C2 to C6 olefins, e.g. ethylene, propylene, butenes, cyclohexene, or mixture thereof, with a low molecular weight C1 to C10, preferably C3 to C10 saturated hydrocarbon and/or to produce branched products containing 1 to 10, preferably 1 to 6, even more preferably 2 to 6 additional carbon atoms. For example, the reaction of one or more C2 to C6 olefins with one or more C3 to C10 hydrocarbons provides a product comprising one or more branched C5 to C12 hydrocarbons. The branched hydrocarbons and C3 to C6 alcohols of this invention often have a composite octane number greater than 80, or even greater than 85, or even greater than 90. The high octane number of such branched products makes them useful as fuel or as octane boosting additives in motor fuel.

In one exemplary reaction, reacting ethylene and isobutane provides a reaction mixture including dimethyl butane and trimethyl pentane In another exemplary reaction, reacting ethylene and propane, both linear compounds, provides a product comprising isopentane, dimethyl pentanes, and trimethyl hexanes, which are all branched products. In such reaction schemes smaller products, e.g., C7 and smaller, or even C6 or smaller, or even C5 and smaller, or even C4 and smaller can be recycled for re-processing to increase the production of branched C8 to C12 materials, as the C8 to C12 materials may be more suitable for use as additives to boost octane.

A useful indicator of the efficiency of free radical reactions is the ratio (efficiency ratio) of the total weight of the resultant products to the total amount of initiator(s) supplied to the reaction. Generally, a greater ratio indicates higher efficiency. Many conventional processes are characterized by an efficiency ratio of 10 or less or even 5 or less. As a significant advantage, many methods of the present invention provide efficiency ratios of 10 or more, even 50 or more, or even 60 or more. This means that the composite weight of the resultant products exceeds ten times, even fifty times or even sixty times the weight of initiator used. As a further advantage, the composite yields of products typically not only exceeds the initiator by over tenfold and often times fifty fold by weight, even over sixty fold but also produces a desirable product mixture for which a major portion is the lower molecular weight C3 to C24, preferably C3 to C12 products.

Also of significance, the literature suggests that chain transfer is a poor reaction strategy for an alcohol such as methanol or other reactants with C—H bond strengths in the 93 kcal/mol to 97 kcal/mol regimes (as measured at 298 K). Advantageously, the present invention provides reaction features that facilitate effective chain transfer for these reactants. This is accomplished in part by using a large stoichiometric excess of the saturated reactant, using low amounts of initiator, and maintaining a high consumption rate of the unsaturated in the reaction zone such that overall conversion of the unsaturated reactant is high (such as by running the reaction at higher temperatures or pressures, by using active initiators such as an initiator having a 10 minute to 3 hour half-life at 140° C.). Advantageously, these features help to enhance chain transfer more than would be expected according to conventional knowledge.

For purposes of illustration, principles of the present invention will now be illustrated with respect to a reaction between isobutane and ethylene, wherein the ethylene concentration is maintained at less than 3 weight percent, preferably less than 2 weight percent, preferably less than 1.5 weight percent, or even about 1 weight percent based on the total weight of ethylene and isobutane. For purposes of illustration, DTBP is used as the initiator. Overall, the reaction between isobutane and ethylene may be represented by the following reaction, wherein the resultant product is a mixture that includes but is not limited to the two illustrative, branched products:

Isobutane+ethylene→dimethyl butane+trimethyl pentane(isooctane)    (3)

The free radical reaction may be represented by a reaction pathway shown in Table 3 including reaction steps 1 to 10:

TABLE 3

| | | Reaction scheme for isobutane and ethylene |
|---|---|---|
| 1 | Initiation | DTBP + Δ → 2 TBP* |
| 2 | Initiation | TBP* + (CH$_3$)$_3$CH → *C(CH$_3$)$_3$ + TBuOH |
| 3 | Propagation | *C(CH$_3$)$_3$ + CH$_2$=CH$_2$ → (CH$_3$)$_3$CCH$_2$CH$_2$* |
| 4 | Chain Transfer | (CH$_3$)$_3$CCH$_2$CH$_2$* + (CH$_3$)$_3$CH → (CH$_3$)$_3$CCH$_2$CH$_3$ + *C(CH$_3$)$_3$ |
| 5 | Chain Transfer | (CH$_3$)$_3$CCH$_2$CH$_3$ + (CH$_3$)$_3$CCH$_2$CH$_2$* → (CH$_3$)$_3$CCH$_2$CH$_3$ + (CH$_3$)$_3$CC*H(CH$_3$) |
| 6 | Propagation | (CH$_3$)$_3$CC*H(CH$_3$) + CH$_2$=CH$_2$ → (CH$_3$)$_3$CCH(CH$_3$)CH$_2$CH$_2$*) |
| 7 | Chain Transfer | (CH$_3$)$_3$CCH(CH$_3$)CH$_2$CH$_2$*) + (CH$_3$)$_3$CH → (CH$_3$)$_3$CCH(CH$_3$)CH$_2$CH$_3$ + *C(CH$_3$)$_3$ |
| 8 | Olefin addition | (CH$_3$)$_3$CCH$_2$CH$_2$* + CH$_2$=CH$_2$ → (CH$_3$)$_3$CCH$_2$CH$_2$CH$_2$CH$_2$* |
| 9 | Chain Transfer | 1. (CH$_3$)$_3$CCH$_2$CH$_2$CH$_2$CH$_2$* + (CH$_3$)$_3$CH → *C(CH$_3$)$_3$ + (CH$_3$)$_3$CCH$_2$CH$_2$CH$_2$CH$_3$ |
| 10 | Termination | Radical combination or disproportionation |

Steps 4, 5, 7 & 9 in Table 3 are chain transfer steps inter-molecularly. Although not shown, chain transfer also can occur intra-molecularly. Steps 3 and 6 represent olefin addition and precede product formation in steps 4 and 7. Step 8 chain extension generally is undesirable and would be favored by higher ethylene concentration. Although not shown, radical combination leads to higher molecular weight highly branched products and can lower yield. It is expected that steps 3 and 4 dominate the process with steps 5 through 9 occurring to a small extent. Recycle of 2,2-dimethyl butane leads to more production of 2,2,3-trimethyl pentane as desired.

In summary, the reaction steps shown in Table 3 include four desirable main steps: initiation, propagation, chain transfer and termination. As practices using principles of the present invention, these steps lead to a product mixture comprising highly branched products of low molecular weight. These desirable products tend to include the addition of 2 to 4 carbons from ethylene to each isobutane. The number of added carbons will depend on the unsaturated reactant that is used. For example, using propylene would provide products including those with 3 or 6 carbon atoms added to each isobutene.

The reaction scheme of Table 3 illustrates the advantages of using a low concentration range of olefin in the reaction zone. Higher concentrations of olefin above 3 wt % would tend to lead to too many chain extension steps. More linear products with an undesirable wide product molecular weight distribution would result. Maintaining a low yet sufficient concentration of olefin in reaction zones allows chain transfer to dominate, which facilitates formation of the most stable secondary and tertiary free radicals. The present invention teaches how running a free radical reaction process with the unsaturated reactant present at a sufficiently low concentration is able to promote chain transfer yet be sufficient to sustain the catalytic process. An unexpected outcome is the improved yield of more highly branched radicals, which in turn lead to more highly branched, higher octane hydrocarbon products.

The ability to practice the reaction steps of Table 1 in a manner that improves production of branched C5 to C12 species is unexpected. Typically, it has been conventional wisdom that a hydrocarbon radical R* in the presence of a hydrocarbon and an olefin has three primary potential reaction pathways:
1. Olefin addition—R*+CH$_2$=CH$_2$→RCH$_2$CH$_2$* [Also termed chain extension]
2. Chain Transfer—R*+(CH$_3$)$_3$CH→RH+(CH$_3$)$_3$C* [Formation of a more stable radical.]
3. Radical combination—R*+R*→R$_2$ Generally all three of these reactions are energetically favorable (exothermic). Olefin addition and radical combination go quite efficiently, since these reactions have little if any energy of activation. Conversely, chain transfer reactions are less efficient, since they involve a hydrogen transfer and are known to have a higher energy of activation. In the meantime, tertiary alkyl radicals (those on a carbon with three carbons attached) are more stable than secondary alkyl radicals (those on a carbon with two carbons attached), which in turn are more stable than primary radicals (those on a carbon with one carbons attached).

According to conventional wisdom, the reaction step efficiency is thought to be the product of individual reaction collision probability (RCP) and the reaction effectiveness factor (REF). Experimental data and conventional wisdom indicate that the REF for radical olefin addition is near 1 and that the REF for chain transfer a carbon hydrogen bond could be as low as 0.01. Given this situation, it would appear that improving production of branched C5 to C12 products from the reaction of C2 to C6 olefin and C3 to C10 hydrocarbon would be extremely challenging.

Contrary to this conventional wisdom, it has surprisingly been found that the RCP chain transfer (RCPct) can be maintained quite high relative to the RCP olefin addition (RCPoa) at high overall alkane and olefin conversion, if the olefin is kept at a sufficiently low concentration in the reaction zone and it is reacted at a rate equal or greater than the rate at which olefin fed (i.e., the feed rate is equal to or lower than the consumption rate). Contrary to prior art technologies, there is no restriction on the ratio of olefin to alkane being fed so long as the unsaturated reactant is fed at a rate such that its steady state concentration in the reactor zone is kept in the 100 ppm to 3 wt % range. In fact in one mode of the invention, only olefin and initiator could be fed such that a controlled increase in molecular weights of the resultant products could be achieved. Uniquely, the olefin addition reaction occurs predominately on the more stable chain transfer radicals. This factor results in production of olefin addition products, which are more highly branched.

By way of illustration and with reference to Table 2 shown above, a reaction mixture containing $(CH_3)_2CHCH_2CH_3$ (isopentane) and $CH_2=CH_2$(ethylene) illustrates principles of the present invention. Isopentane has one tertiary C—H bond and two secondary H—C—H bonds. Assuming the overall REF for chain transfer (REFct) is about 0.01, then the REF for olefin addition (REFoa), or chain transfer, starts to be competitive with olefin addition at about 3 wt % ethylene. Chain transfer becomes the dominate process at lower ethylene concentrations. There is generally a lower desired limit for ethylene concentration in order to maintain a catalytic process. Although Table 2 is generated for ethylene and isopentane, the trends shown in Table 2 are generically applicable for any C2 to C4 olefin or mixtures thereof.

In order to favor chain transfer over olefin addition and thereby limit molecular weight build up associated with chain extension, the data in this table indicates that olefin concentration in the reaction zone of the invention should be in the 100 ppm to 3 wt % range, preferably 100 ppm to 1.2 weight percent. The product mix and reaction rate could be controlled adjusted by controlling the steady state concentration of the olefin during the reaction. Again there is no restriction on the ratio olefin to alkane ratio fed, only that it be fed at a rate that it's steady state concentration in the reactor is kept in the 100 ppm to 3 wt % range. In fact in one mode of the invention, only olefin could be fed such that a controlled increase in molecular weight of the starting alkane could be achieved. Uniquely, the olefin addition reaction occurs predominately on the more stable chain transfer radicals rather than what is observed in the prior art. This factor results in production of olefin addition products, which are more highly branched.

As another example of the present invention, the following reaction pathway uses ethylene, propane and catalytic DTBP:
1. Initiation: DTBP+Δ→2 TBP*
2a. Initiation: TBP*+$CH_3CH_2CH_3$→$CH_3CH_2CH_2$*+ TBuOH (Note 6 primary C—H and 2 secondary H)
2b. Initiation: TBP*+$CH_3CH_2CH_3$→*$CH(CH_3)_2$+ TBuOH secondary C—H on propane.
3. Chain Transfer: $CH_3CH_2CH_2$*+$CH_3CH_2CH_3$→*CH$(CH_3)_2$+$CH_3CH_2CH_3$ (Chain transfer ("CT") to more stable radical.)
4. Olefin Addition: *$CH(CH_3)_2$+$CH_2=CH_2$→$(CH_3)_2CHCH_2CH_2$*
5. Chain Transfer: $(CH_3)_2CHCH_2CH_2$*+$(CH_3)_2CH_2$→ $(CH_3)_2CHCH_2CH_3$+*$CH(CH_3)_2$
6. Propagation: Repeat steps 4 & 5
7a. Olefin Addition $CH_3CH_2CH_2$*+ $CH_2=CH_2$→$CH_3CH_2CH_2CH_2CH_2$* (Olefin addition w/o CT)
7b. Olefin Addition $(CH_3)_2CHCH_2CH_2$*+$CH_2=CH_2$→ $(CH_3)_2CHCH_2CH_2CH_2CH_2$* (Olefin addition w/o CT)
8. Chain Transfer $(CH_3)_2CHCH_2CH_2$*+$(CH_3)_2CH_2$→ $(CH_3)_2CHCH_2CH_3$+$CH_3CH_2CH_2$*

(Termination: Radical combination or disproportionation)

Initially steps 2a and 2b likely occur as both highly energetically favorable. At low ethylene concentration chain transfer reaction 3 will be favored to occur over olefin addition step 7a. Under chain transfer favorable conditions, olefin addition will eventually occur to the most stable radicals, e.g., step 4. The radical product of step 4 will either form product through chain transfer step 5 or undergo olefin addition step 7b. Note primary to primary chain transfer steps such as step 8 are not energetically favorable, as such do not occur to an appreciable extent. At a preferred olefin concentration of 100 ppm to 1%, it is expected that steps 4 and 5 will dominate the process. Although not shown, radical combination leads to higher molecular weight, highly branched products. It is desirable to have a sufficient, but steady low concentration of radical initiator, hence the desire to run continuously at steady state conditions. Overall the reaction between propane and ethylene becomes:

Propane+ethylene→2-methyl butane(isopentane)

The product mix depends on the amount of ethylene fed (conversion) and/or selective recycle of products. Hence isopentane could become a primary feed. The olefin only can be fed at a rate and concentration such that chain transfer is favored over olefin addition. Ultimately the reaction between propane and ethylene, assuming significant isopentane recycle, becomes:

Propane+ethylene→isopentane+dimethyl pentanes+ trimethyl hexanes

The above illustrations show how branched products may result using ethylene as an unsaturated reactant. Addition of ethylene may generate a primary radical ($RCH_2CH_2$*) in the course of the chain reactions. Even though ethylene is linear and a co-reactant such as propane also may be linear, a branched product still results because ethylene can add onto a secondary propane radical. In other words, a bond forms between the added ethylene residue and the middle or secondary carbon of the propane radical. There is a difference between adding ethylene to a radical, which tends to generate a primary radical upon ethylene addition, and adding any substituted olefin such as propylene to the same radical R*. Adding any substituted olefin such as propylene to a radical R* generates a secondary radical ($RCH_2C$*$HCH_3$). Hence, branching can result when adding a substituted olefin such as propylene to any primary, secondary, or tertiary radical because the propylene residue itself is branched. The secondary radical resulting from propylene or similar substituted olefin addition then tends to undergo chain transfer from tertiary carbons on a co-reactant radical, thus being less reactive overall than ethylene and likely to be useful in some applications. For example, this could be useful if you desired adding propylene only to the tertiary or most reactive site of the chain transfer agent.

In one illustrative embodiment the invention involves reacting at least one hydrogen and carbon containing compound with at least one C2 to C4 olefin that is in the liquid phase, gas and/or supercritical phase in the in the presence of at least one free radical initiator at a temperature above 30° C. and a pressure above atmospheric. Primary reaction in the liquid phase is preferred although reaction in multiple phases may be desirable. The present invention allows the formulation of the product mixture to be controlled primarily by controlling the total C2 to C4 steady state olefin concentration to be less than 3 weight percent by controlling the rate of olefin feed to be ~ equal to or less than its reaction rate in one or more reaction zones. Preferably the desirable concentration of olefin in the reaction zone is in the 10 ppm to 3 weight percent range and more preferably in the 100 ppm to 1 weight percent range. Generally speaking greater than 3 weight percent olefin in the reaction zone leads to undesirable chain extension. Also, olefin concentrations below 100 ppm in the reaction zone lead to undesirable low process productivity.

It may be desirable to selectively recycle some of the product output in some cases. For example, if C6 or larger product species are desired, smaller species may be recycled for re-processing.

In another preferred embodiment of the invention involves reacting predominately one hydrogen and carbon containing compound with predominately one olefin in the presence of at least one free radical initiator to selectively produce predominately one product in which the starting hydrogen and carbon containing compound is increased by the incorporation of one molecule of olefin. The preferred olefin is ethylene or propylene with ethylene being most preferred. The preferred carbon and hydrogen containing compound is any C2 to C8 hydrocarbon or methanol. In this way 1-propanol or 1-butanol can be produced from methanol and ethylene or propylene respectively.

In another preferred embodiment propane, butane, pentane or a mixture thereof is reacted with at least one olefin (preferably ethylene) in the presence of a free radical initiator to produce a high octane branched hydrocarbon mixture useful directly as fuel or as a blending component for fuel.

In another embodiment, a diol such as ethylene glycol or a polyol such as glycerin is reacted with at least one olefin (preferably ethylene) in the presence of a free radical initiator to produce branched alcohols comprising a plurality of OH functional groups.

In some embodiments, the present invention prepares fuel compositions using one or more ingredients comprising natural gas. Raw natural gas can be obtained from one or more natural sources and optionally processed to remove contamination such as acids, mercaptans, water, and the like. Ethylene can be derived from the ethane content of the natural gas. The ethylene may be purified if desired so that the ethylene stream contains more than 80 weight percent, preferably more than 90 weight percent, preferably more than 95 weight percent ethylene based on the total weight of ethylene and ethane. The ethylene can then be used an unsaturated reactant in the practice of the present invention.

In some embodiments, raw natural gas can be obtained from one or more natural sources and optionally processed to remove contamination such as acids, mercaptans, water, and the like. A heavy component can be separated from the natural gas and used as the chain transfer agent in the practice of the present invention. The heavy component may be purified so that one or more C3 to C10 species, preferably C3 and C4 species, constitute at least 50 weight percent, preferably at least 70 weight percent, and more preferably at least 90 weight percent of the reactant composition based on the total weight of the reactant composition.

An important advantage of illustrative modes of practice of the present invention is the ability to selectively insert 1 mole of ethylene and/or propylene productively and per mole of hydrocarbon or oxygen containing hydrocarbon of any size. This provides an easy, economical, and efficient way to add 2 or 3 carbon atoms to such organic compounds. For example, methanol, ethanol and/or isobutene can be reacted with ethylene and/or propylene to increase the molecule size by 2 carbon atoms upon reaction with ethylene or 3 carbon atoms upon reaction with propylene. For example, propanol is in high demand; and improved ways to make propanol from raw materials are needed. The present invention fills that need. Specifically limiting the ethylene concentration of the reaction zone in accordance with the present invention, ethylene and methanol can be reacted using principles of the present invention to produce n-propanol. Similarly, ethylene can be reacted with ethanol to provide 2-butanol. Propylene can be reacted with methanol to provide n-butanol. Propylene can be reacted with ethanol to provide 2-pentanol.

The present invention will now be further described with reference to the following illustrative examples.

Example 1

This example shows reaction conditions of the present invention that help to provide limited and linear addition of ethylene to 2,3-dimethyl butane. A Teflon lined 300 cc autoclave equipped with an internal Teflon stirrer, and Teflon coated internals (ethylene feed tube, liquid sample tube and thermo well) was evacuated under mild vacuum and purged twice with nitrogen. The resulting reactor having an internal volume of ~240 ml was charged with 100 g of 2,3-dimethyl butane and 0.3 g dissolved DTBP (ditertiary butyl peroxide). The reactor was pressurized with ethylene to 300 psig and vented twice and pressurized a third time to 300 psig with ethylene. The initial reaction liquid temperature was 17° C. with a stirring rate of ~200 rpm (Sample 1-A and all other samples were removed through the liquid sample tube and collected in a chilled vial). The reactor liquid was brought to ~141° C. and held there for a total reaction time of 90 minutes. The reaction pressure was ~720 psig. Additional ethylene was added from time to time to make up for consumed ethylene during this time at ~141° C. and also later at subsequent reaction temperatures. After sample 1-B was taken, the reactor was taken to ~157° C. and held there for a total reaction time of 190 minutes. After sample 1-C was taken, the reactor was taken to ~165° C. and held there for a total reaction time of 235 minutes. After sample 1-D was taken the reactor was held at temperature for an additional 15 minutes and allowed to cool to room temperature overnight. Sample 1-E was taken at this time. A run summary is shown is shown below in Table 4.

TABLE 4

2,3-Dimethyl Butane/Ethylene Run Table 1: Ethylene Partial Pressure = ~300 psig

| Sample | Total Rxtn Time minutes | Rxtn Temp ° C. | Wt % Alkanes | | | | | | | | | Est. C8 % Efficiency |
| --- | --- | --- | --- | --- | --- | --- | --- | --- | --- | --- | --- | --- |
| | | | C6 | C8 | C10 | C12 | C14 | C16 | C18 | Total C20 to C30 | ¯Total | |
| 1-A | 0 | 20 | 99.6 | 0 | 0 | 0 | 0 | 0 | 0 | 0 | 1.01 | 11 |
| 1-B | 90 | ¯141 | 97.8 | 0.11 | 0.12 | 0.11 | 0.11 | 0.09 | 0.09 | 0.38 | 1.01 | 11 |
| 1-C | 190 | ¯157 | 93.8 | 0.38 | 0.36 | 0.37 | 0.32 | 0.27 | 0.27 | 1.08 | 3.05 | 12 |
| 1-D | 235 | ¯165 | 93.0 | 0.43 | 0.41 | 0.41 | 0.34 | 0.30 | 0.29 | 1.24 | 3.42 | 13 |
| 1-E* | ¯250 | <160 | 93.8 | 0.36 | 0.34 | 0.31 | 0.28 | 0.26 | 0.24 | 1.07 | 2.86 | 13 |

Charged 100 g 2,3-Dimethyl Butane + 0.3 g DTBP Ethylene Partial Pressure = ¯300 psig @ 20° C.
*Sampled at room temperature.

Noting that the C6 column represents the starting material dimethyl butane, primarily C8 (8 carbon) through C30 (30 carbon) even numbered, branched hydrocarbons were produced. The C8 product was mainly of two products, each resulting from incorporation of one ethylene with the C6 2,3-dimethyl butane starting alkane. The total C8 product amounted to about 13% of the total hydrocarbon products. About 37% of the total product was heavy C20 to C30 hydrocarbons. In this example, the ethylene concentration was high.

Example 2

This example shows reaction conditions of the present invention that help to provide limited and linear addition of ethylene to 2,3-dimethyl butane. A Teflon lined 300 cc autoclave equipped with an internal Teflon stirrer, and Teflon coated internals (ethylene feed tube, liquid sample tube and thermo well) was evacuated under mild vacuum and purged twice with nitrogen. The resulting reactor having an internal volume of ~240 ml was charged with 133 g of 2,3-dimethyl butane and 0.3 g dissolved DTBP (ditertiary butyl peroxide). The reactor was pressurized with ethylene to 80 psig and vented twice and then pressurized a third time to 80 psig with ethylene. The initial reaction liquid temperature was 23° C. with a stirring rate of ~200 rpm. Sample 2-A was taken from this initial reaction mixture. (Sample 2-A and all other samples were removed through the liquid sample tube and collected in a chilled vial). The reactor liquid was brought to ~142° C. and held there for a total reaction time of 30 minutes, not including heat up time. The reaction pressure was ~400 psig. Additional ethylene was added from time to time to maintain ethylene partial pressure and to make up for consumed ethylene during this time at ~142° C. and later at subsequent reaction temperatures. After sample 2-B was taken the reactor was taken to ~147° C. and held there for a total reaction time of 105 minutes. After sample 2-C was taken the reactor was taken to ~152° C. and held there for a total reaction time of 175 minutes. After sample 2-D was taken the reactor was taken to ~160° C. held at temperature for a total reaction time of 265 minutes. After sample 2-E was taken the reactor was heated 165° C. an additional 15 minutes and allowed to cool to room temperature overnight. Sample 2-F was taken at this time. A run summary is shown in Table 5:

Noting that the C6 column represents the starting material, primarily C8 (8 carbon) through C30 (30 carbon) even numbered, branched hydrocarbons were produced. The C8 product was mainly of two products, each resulting from incorporation of one ethylene with the C6 2,3-dimethyl butane starting alkane. The total C8 product amounted to about ~29% of the total hydrocarbon products. About 7% of the total product was heavy C20 to C30 hydrocarbons.

Example 3

According to a preferred mode a Teflon lined 300 cc autoclave equipped with an internal Teflon stirrer, and Teflon coated internals (ethylene feed tube, liquid sample tube and thermo well) was evacuated under mild vacuum and purged twice with nitrogen. The resulting reactor having an internal volume of ~240 ml was charged with 120 g of isopentane and 0.3 g dissolved DTBP (ditertiary butyl peroxide). The reactor was pressurized with ethylene to 30 psig, vented and pressurized again to 30 psig with ethylene. The initial reaction liquid temperature was 17° C. with a stirring rate of 120 rpm (Sample 3-A and all other samples were removed through the liquid sample tube and collected in a chilled vial). The reactor was brought to ~146° C. and held there for a total reaction time of 60 minutes. The reaction pressure was ~285 psig. Additional ethylene was added from time to time to make up for consumed ethylene during this time at 146° C. and later at subsequent reaction temperatures. After sample 3-B was taken the reactor was taken to ~152° C. and held there for a total reaction time of 125 minutes. After sample 3-C was taken the reactor was taken to ~158° C. and held there for a total reaction time of 195 minutes. After sample 3-D was taken the reactor was taken to ~164° C. and held there for a total reaction time of 235 minutes. After sample 31-E was taken the reaction was continued and held there for a total reaction time of 300 minutes. The reaction was allowed to cool overnight and Sample 3-F was taken. A run summary is shown in Table 6, where the C5 column represents the starting material.

TABLE 5

2,3-Dimethyl Butane/Ethylene Run Table 2: Ethylene Partial Pressure = ~80 psig
2,3-Dimethyl Butane/Ethylene Batch Reaction

| Sample | Total Rxtn Time minutes | Rxtn Temp ° C. | Wt % Alkanes | | | | | | | Total C20 to C30 | Total | Est. C8 % Efficiency |
|---|---|---|---|---|---|---|---|---|---|---|---|---|
| | | | C6 | C8 | C10 | C12 | C14 | C16 | C18 | | | |
| 2-A | 0 | 20 | 99.6 | ? | 0 | 0 | 0 | 0 | 0 | 0 | | |
| 2-B | 30 | ~142 | 99.1 | 0.21 | 0.073 | 0.054 | 0.042 | 0.025 | 0.021 | 0.02 | 0.445 | 47 |
| 2-C | ~105 | ~147 | 98.0 | 0.27 | 0.22 | 0.21 | 0.12 | 0.06 | 0.05 | 0.07 | 1.00 | 27 |
| 2-D | ~175 | ~152 | 96.9 | 0.43 | 0.36 | 0.34 | 0.21 | 0.11 | 0.07 | 0.12 | 1.64 | 26 |
| 2-E | ~265 | <160 | 95.8 | 0.66 | 0.49 | 0.45 | 0.32 | 0.13 | 0.11 | 0.15 | 2.31 | 29 |
| 2-F* | ~280 | 165 | 95.99 | 0.56 | 0.44 | 0.40 | 0.27 | 0.13 | 0.11 | 0.14 | 2.05 | 28 |

Charged 133 g 2,3-Dimethyl Butane + 0.3 g DTBP Ethylene Partial Pressure ~80 psig @ 20° C.

Sample 2-E ~10 g product per 1.0 g DTBP

*Sampled at room temperature.

TABLE 6

Isopentane/Ethylene Batch [0.3% DTBP]

| Sample | Total Rxtn Time minutes | Rxtn Temp ° C. | Rxtn Pressure psig | Wt % Alkanes | | | | | C7(%) | C9(%) | C7 + C9(%) |
|---|---|---|---|---|---|---|---|---|---|---|---|
| | | | | C5 | C7 | C9 | C11 | Total | | | |
| 3-A | 0 | −17 | 30 | 99.8 | | | | | | | |
| 3-B | 60 | −146 | −285 | 98.67 | 0.40 | 0.042 | 0.014 | 0.456 | 88 | 9 | 97 |
| 3-C | −125 | −152 | −305 | 98.8 | 0.568 | 0.068 | 0.018 | 0.654 | 86 | 11 | 97 |
| 3-D | −195 | −158 | −330 | 97.6 | 0.85 | 0.18 | 0.07 | 1.10 | 77 | 17 | 94 |
| 3-E | −235 | −164 | −360 | 97.68 | 1.026 | 0.202 | 0.073 | 1.301 | 79 | 16 | 95 |
| 3-F | −320 | −20 | −370 | 96.59 | 1.41 | 0.40 | 0.18 | 1.99 | 71 | 20 | 91 |

Achieved 8 g product per 1 g DTBP. Ethylene pressure adjusted as run progressed and extra 30 psi after sample 3E. Stucture of products validated by GC MS. The C7 hydrocarbon alkane was a mixture of 3,3-dimethyl pentane and 2,3-dimethyl pentane. The C9 hydrocarbon was primarily 3,3,4-trimethyl hexane. Estimated RON (research octane number) of the product mixture is greater than 95 (Ind. Eng. Chem. Res. 2006, 45, 337-345).

The ethylene concentration in Sample 3-F was 0.11%. A gas sample from the reactor showed ~65% isopentane and 31% ethylene. The product incorporating only 1 mole of ethylene per mole of starting hydrocarbon was ~80%, while the total product incorporating 1 or 2 moles of ethylene per mole of starting hydrocarbon was ~95%.

Example 4

According to a preferred mode, a Teflon lined 300 cc autoclave is equipped with a preheated liquid feed line, an ethylene feed line and a reactor over flow line which is routed to a chilled liquid product Hoke collection vessel equipped with a back pressure regulator. The resulting reactor having an internal volume of ~240 ml is charged with ~150 g of isopentane containing 0.75 g DTBP. A nitrogen blanketed liquid feed tank is charged with 1500 g of isopentane containing 1.5 g (0.10%) of ditertiary butyl peroxide (DTBP). The isopentane feed containing DTBP is initiated at rate of 3.6 g (50 mmol) per minute through the liquid feed line preheated to 130° C. The back pressure regulator is set to 500 psig and the reactor is brought to ~160° C. Ethylene flow is initiated at ~110 sccm, 5 mmol per minute. The run was conducted for approximately 6.5 hours with the conditions and composite liquid product samples taken ~every 40 minutes from the Hoke collection vessel. The last liquid product sample contained over 10 wt % of 3,3-dimethyl pentane, 2,3-dimethyl pentane and 3,3,4-trimethyl hexane. The product efficiency to C7 plus C9 hydrocarbons was over 90%.

Example 5

According to a preferred mode, a Teflon lined 300 cc autoclave equipped with an internal Teflon stirrer, infrared cell and Teflon coated internals (ethylene feed tube, liquid sample tube and thermo well) would be evacuated under mild vacuum and purged twice with nitrogen. The resulting reactor having an internal volume of ~240 ml would be charged with 165 g of methanol and 0.3 g dissolved DTBP (ditertiary butyl peroxide). The reactor would be pressurized with ethylene to 30 psig, vented and pressurized again to 30 psig with ethylene. The initial reaction liquid temperature would be 20° C. with a stirring rate of 100 rpm. The infrared cell would be calibrated to give a measure of the concentration of the ethylene in the liquid phase of the reactor. Samples would be removed through the liquid sample tube and collected in a chilled vial. The reactor would be brought to ~150° C. and held there for a total reaction time of 60 minutes. Additional ethylene would be added from time to time at this temperature and subsequently to maintain the dissolved ethylene in the liquid phase to be in the 0.1 wt % to the 1 wt % range. The reactor would be taken first to ~160° C. for 30 minutes and then ~170° C. for an additional 30 minutes. A representative liquid sample would be taken initially and after each reaction temperature. Normal propanol and 1-pentanol would be the major products in all liquid samples and would amount to greater than 95% of the total alcohol products.

Example 6

Conducting reaction of other alcohols with either ethylene or propylene in like fashion to example 5 would result in incorporation of 1 olefin molecule as the major product in all cases. The other alcohols would include each of the following, respectively: ethanol, n-propanol, i-propanol, n-butanol, i-butanol, n-pentanol, n-hexanol, neopentyl glycol, ethylene glycol, glycerin, 2-pentanol, 3-pentanol, 2-methyl butanol, cyclopentanol, cyclohexanol, benzyl alcohol, sorbitol, 1,3-propanediol, butane diols, hexane diols and the like.

Example 7

Example 5 is repeated, except propylene would be used for ethylene.

Example 8

Example 6 is repeated, except propylene would be used for ethylene.

Example 9

Example 5 is repeated, except a mixture of ethylene and propylene at a 1:1 ratio is used.

Example 10

Example 6 is repeated, except a mixture of ethylene and propylene at a 1:1 ratio is used.

All patents, patent applications, and publications cited herein are incorporated herein by reference in their respective entities for all purposes. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A continuous method of making one or more $C_3$ to $C_{12}$ organic compounds, comprising the step of free radically reacting reactants comprising at least one $C_2$ to $C_6$ unsaturated organic compound and at least one $C_1$ to $C_{10}$ chain transfer agent in a reaction zone in the presence of at least one free radical initiator under conditions effective to form a reaction product comprising the one or more $C_3$ to $C_{12}$ organic compounds, wherein:
   i) the at least one $C_2$ to $C_6$ unsaturated organic compound is fed to the reaction zone in a manner effective to limit the concentration of the at least one $C_2$ to $C_6$ unsaturated organic compound in the reaction zone to 2 weight percent or less based on the total weight of the at least one $C_2$ to $C_6$ unsaturated organic compound and the at least one chain transfer agent in the reaction zone;
   ii) the at least one $C_2$ to $C_6$ unsaturated organic compound is reacted in the reaction zone at a rate equal to or greater than the rate at which the at least one $C_2$ to $C_6$ unsaturated organic compound is fed to the reaction zone; and
   iii) the at least one $C_2$ to $C_6$ unsaturated organic compound and the at least one $C_1$ to $C_{10}$ chain transfer agent are reacted in the reaction zone in a manner such that the molar conversion of the at least one $C_2$ to $C_6$ unsaturated organic compound is greater than the molar conversion of the at least one $C_1$ to $C_{10}$ chain transfer agent.

2. The method of claim 1, wherein the at least one $C_2$ to $C_6$ unsaturated organic compound comprises ethylene.

3. The method of claim 2, wherein the at least one chain transfer agent comprises methanol and the product comprises 1-propanol.

4. The method of claim 2, wherein the chain transfer agent comprises isobutane and the product comprises dimethyl butane and trimethyl pentane.

5. The method of claim 1, wherein the at least one $C_2$ to $C_6$ unsaturated organic compound comprises propylene.

6. The method of claim 5, wherein the at least one chain transfer agent comprises methanol and the product comprises 1-butanol.

7. The method of claim 1, wherein the at least one $C_2$ to $C_6$ unsaturated organic compound comprises a hydrocarbon and wherein the at least one chain transfer agent comprises a hydrocarbon.

8. The method of claim 1, wherein the molar ratio of the at least one $C_2$ to $C_6$ unsaturated organic compound to the total moles of the at least one free radical initiator fed to the reaction is in the range from 40:1 to 2000:1.

9. The method of claim 1, wherein the concentration of the at least one $C_2$ to $C_6$ unsaturated organic compound in the reaction zone is in the range from 10 ppm to 1.2 weight percent based on the total weight of the at least one $C_2$ to $C_6$ unsaturated organic compound and the at least one chain transfer agent in the reaction zone.

10. The method of claim 1, wherein the steady state weight ratio of the at least one chain transfer agent to the at least one $C_2$ to $C_6$ unsaturated organic compound in the reaction zone is higher than the feed weight ratio.

11. The method of claim 1, further comprising recovering one or more desired products from the product and recycling a remainder to the reaction zone.

12. The method of claim 1, wherein the reaction occurs in a reaction vessel in which the surface to volume ratio is less than $0.5\ cm^{-1}$.

13. The method of claim 1, wherein the reaction zone includes a surface that comprises one or more of a fluoropolymer, quartz, a nitride, a carbide, and combinations of these.

14. The method of claim 1, wherein the step of free radically reacting the reactants comprises free radically reacting the reactants in a plurality of reaction zones, and wherein the concentration of the at least one $C_2$ to $C_6$ unsaturated organic compound in the reaction zone is 2 weight percent or less based on the total weight of the at least one $C_2$ to $C_6$ unsaturated organic compound and the at least one chain transfer agent in one or more reaction zones.

15. The method of claim 1, wherein metal is excluded from the reaction zone.

16. The method of claim 1, wherein the reaction zone has surfaces in contact with the at least one of ethylene and/or propylene and the at least one $C_1$ to $C_{10}$ alcohol reactant and wherein the surfaces are substantially inert with respect to the at least one of ethylene and/or propylene and the at least one $C_1$ to $C_{10}$ alcohol reactant.

17. A method of making one or more $C_3$ to $C_{12}$ alcohols, comprising the step of free radically reacting reactants comprising at least one of ethylene and/or propylene and at least one $C_1$ to $C_{10}$ alcohol reactant in a reaction zone in the presence of at least one free radical initiator under conditions effective to form a reaction product comprising the one or more $C_3$ to $C_{12}$ alcohols, wherein:
   i) the concentration of the ethylene if any and propylene if any in the reaction zone is 2 weight percent or less based on the total weight of the ethylene if any and propylene if any and the at least one alcohol reactant in the reaction zone;
   ii) the at least one of ethylene and/or propylene is reacted in the reaction zone at a rate equal to or greater than the rate at which the at least one of ethylene and/or propylene is fed to the reaction zone; and
   iii) the at least one of ethylene and/or propylene and the at least one $C_1$ to $C_{10}$ alcohol reactant are reacted in the reaction zone in a manner such that the molar conversion of the at least one of ethylene and/or propylene is greater than the molar conversion of the at least one $C_1$ to $C_{10}$ alcohol reactant.

18. The method of claim 17, wherein the concentration of the ethylene if any and propylene if any in the reaction zone is in the range from 10 ppm to 1.2 weight percent based on the total weight of the ethylene if any and propylene if any and the at least one chain transfer agent in the reaction zone.

* * * * *